United States Patent [19]

Torobin

[11] Patent Number: 4,743,545
[45] Date of Patent: * May 10, 1988

[54] HOLLOW POROUS MICROSPHERES CONTAINING BIOCATALYST

[76] Inventor: Leonard B. Torobin, Materials Technology Corporation, Tower Place/Suite 1425, 3340 Peachtree Rd., NE., Atlanta, Ga. 30026

[ * ] Notice: The portion of the term of this patent subsequent to Jan. 20, 2004 has been disclaimed.

[21] Appl. No.: 657,090

[22] Filed: Oct. 3, 1984

Related U.S. Application Data

[60] Continuation-in-part of Ser. No. 639,126, Aug. 9, 1984, Pat. No. 4,671,909, which is a continuation-in-part of Ser. No. 428,923, Sep. 30, 1982, Pat. No. 4,548,196, which is a continuation of Ser. No. 103,113, Dec. 13, 1979, abandoned, which is a division of Ser. No. 59,296, Jul. 20, 1979, abandoned, which is a continuation-in-part of Ser. No. 937,123, Aug. 28, 1978, abandoned, and Ser. No. 944,643, Sep. 21, 1978, abandoned.

[51] Int. Cl.$^4$ .................. C12P 1/00; C12N 11/14; G01N 33/551; C07K 17/14
[52] U.S. Cl. .................. 435/41; 435/176; 435/182; 435/288; 435/240.241; 435/240.22; 436/524; 530/811
[58] Field of Search ............. 435/41, 176, 178, 180, 435/182, 288, 240; 436/524, 525, 527; 502/7, 8, 9, 10, 506; 428/402.2, 402.21; 530/811

[56] References Cited

U.S. PATENT DOCUMENTS

| | | | |
|---|---|---|---|
| 3,264,073 | 8/1966 | Schmitt | 29/182 |
| 3,423,489 | 1/1969 | Arens et al. | 264/4 |
| 3,528,809 | 9/1970 | Farnand | 75/222 |
| 3,674,461 | 7/1972 | Farnand | 75/5 R |
| 3,792,136 | 2/1974 | Schmitt | 264/44 |
| 4,059,423 | 11/1977 | DeVos et al. | 65/21 |
| 4,111,713 | 9/1978 | Beck | 106/288 B |
| 4,153,510 | 5/1979 | Messing et al. | 435/176 |
| 4,214,020 | 7/1980 | Ward et al. | 427/296 |
| 4,222,977 | 9/1980 | Dobo | 264/63 |
| 4,230,463 | 10/1980 | Henis et al. | 55/16 |
| 4,257,798 | 3/1981 | Hendricks et al. | 65/21.4 |
| 4,268,278 | 5/1981 | Dobo et al. | 55/16 |
| 4,275,149 | 6/1981 | Litman et al. | 435/178 X |
| 4,279,632 | 7/1981 | Frosch et al. | 65/21.4 |
| 4,303,431 | 12/1981 | Torobin | 65/21.4 |
| 4,303,603 | 12/1981 | Torobin | 264/69 |
| 4,318,988 | 3/1982 | Cabane et al. | 435/176 |
| 4,321,141 | 3/1982 | Messing | 435/176 |
| 4,329,157 | 5/1982 | Dobo et al. | 55/16 |
| 4,344,787 | 8/1982 | Beggs | 65/21.4 |
| 4,348,458 | 9/1982 | Otstot | 428/366 |
| 4,349,456 | 9/1982 | Sowman | 502/8 X |
| 4,352,883 | 10/1982 | Lim | 435/178 |
| 4,415,512 | 11/1983 | Torobin | 264/9 |
| 4,442,216 | 4/1984 | Harvey et al. | 435/176 X |
| 4,448,884 | 5/1984 | Henderson | 435/176 X |

FOREIGN PATENT DOCUMENTS

WO86/01147  2/1986  PCT Int'l Appl. .

OTHER PUBLICATIONS

Cutler et al., Lightweight Proppants for Deep Gas Well Stimulation, TerraTek Engineering, TRE 83-18, Dec. 1983, pp. 21-30.

R. P. Reedy, Selection and Measurement of Microsphere Laser Targets Based on Refraction, Journal of Applied Physics, vol. 47, No. 6, Jun. 1976.

Chibatz, I., Immobilized Enzymes, John Wiley & Sons, N.Y., 1978, pp. 10, 54-60.

*Primary Examiner*—David M. Naff
*Attorney, Agent, or Firm*—Perry Carvellas

[57] ABSTRACT

Biocatalyst such as enzymes or cells are immobilized in hollow porous microspheres for use as bioreactors in biochemical processes. The microspheres are of substantially uniform diameter of 200 to 10,000 microns and of substantially uniform wall thickness of 1 to 1000 microns. Walls of the microspheres are formed of sintered together particles such as inorganic particles. The walls have interconnecting voids that are continuous and extend from outer wall surface to the inner wall surface. The biocatalyst is introduced into the microspheres through macropores in the walls, and then immobilized. Immobilization may be performed by introducing a gel forming material with the biocatalyst and forming a semipermeable gel in situ within the microspheres.

44 Claims, 2 Drawing Sheets

HOLLOW POROUS MICROSPHERES CONTAINING BIOCATALYST

RELATED APPLICATIONS

This application is a continuation-in-part of application Ser. No. 639,126, filed Aug. 9, 1984, now U.S. Pat. No. 4,671,909 titled "Hollow Microspheres Made From Dispersed Particle Compositions and Method and Apparatus for Producing Them," the disclosure of which is incorporated herein in its entirety by reference thereto. The application Ser. No. 639,126 is a continuation-in-part of application Ser. No. 428,923 filed Sept. 30, 1982, which application is a continuation of application Ser. No. 103,113 filed Dec. 13, 1979, which is a divisional of application Ser. No. 059,296 filed July 20, 1979, which is a continuation-in-part of application Ser. Nos. 937,123 and 944,643 filed Aug. 28, 1978 and Sept. 21, 1978, respectively.

The application Ser. No. 428,923 is now U.S. Pat. 4,548,196. The U.S. Ser. Nos. 103,113, 059,296, 937,123 and 944,643 are now abandoned.

BACKGROUND OF THE INVENTION

1. Field of the Invention

This invention relates to novel hollow porous microspheres having the pores thereof closed, e.g. coated, impregnated, sealed, filled or covered with a fluid permeable substance, and to the use of these microspheres for providing a non-rupturable support and protective environment for a biocatalytic substance, e.g. microorganisms, cells, cellular products, enzymes, antibodies, and other biochemically active materials, and to the use of the encapsulated biocatalysts, as bioreactors in biochemical processes.

More particularly, the invention relates to bioreactors, i.e. encapsulated biocatalysts, such as, for example, enzymes, antibodies, hormones, interferons, lymphokines, and other non-living biologically active substances, as well as various living substances, including viruses, bacteria, yeasts, single cells, organelles, cellular masses, tissues, and the like, wherein the encapsulating containers are in the form of non-rupturable hollow porous microspheres wherein the pores are coated, impregnated, sealed, filled, covered, or otherwise closed-off with a fluid permeable gel and/or permselective membrane material; and to the biochemical processes using the novel bioreactors.

2. Discussion of the Prior Art

A bioreactor may be broadly defined as a biocatalyst in a container. The biocatalyst may be any one of a wide variety of chemically active biological substances, such as, for example, enzymes, hormones, antibodies, interferons, lymphokines, and other non-living substances, and living microorganisms, such as bacteria, viruses, yeast, single cells, organelles, cellular masses, tissues, etc.

Traditionally, bioreactors have taken the form of fermentation vats, as in the production of alcohols, sugars and other fermentation products. Recently, as the containers or supports for these biocatalysts porous solid and porous hollow organic and inorganic fibers, and microcapsules have been proposed and have been commercially available. The porous fibers and microcapsules provide the advantage of large surface areas for a small volume and when the biocatalyst is encapsulated in the fiber or microcapsule, a sterile environment. A general discussion relating to the use of bioreactors in biotechnological processes can be found in Science, Vol. 219, Feb. 11, 1983, pp. 728–733, "Bioreactors: Design and Operation," Charles L. Cooney.

As representative of the U.S. Patent art relating to hollow fiber membrane cell culture devices mention can be made of the following: U.S. Pat. Nos. 3,821,087, 3,883,393, 3,997,396, 4,087,327, 4,184,922, 4,189,534, 4,200,689, 4,201,845, 4,266,026, 4,293,654, 4,301,249, 4,440,853 and 4,442,206.

As representative of the U.S. Patent art relating to organic polymeric porous microcapsules for encapsulating various biocatalysts mention can be made of the following: U.S. Pat. Nos. 3,522,346—Chang; 4,349,530—Roper; 4,353,888—Sefton; 4,148,689—Hino, et al; 4,310,554 Olson, et al; 3,767,790 and 3,860,490—Guttag; 4,431,428—Schmer; 4,321,327 Chen, et al; and the following group of patents, all assigned to Damon Corporation: U.S. Pat. Nos. 4,251,387, 4,255,411, 4,257,884, 4,322,311, 4,324,683, 4,352,883, 4,391,909, 4,407,957 and 4,409,331.

There is also a large body of patent art relating to the use of solid beads, which may or may not be porous, on which microorganisms and/or enzymes can be fixed or immobilized. For example, mention can be made of the following U.S. Patents: 4,343,901—DeFilippi; 4,189,534 and 4,293,654—Levine, et al; 4,153,510 Messing; 3,717,551—Bizzini, et al, and others. See also, K. Nilsson, et al., "Entrapment of animal cells for production of monoclonal antibodies and other biomolecules," Nature, Vol. 302, Apr. 14, 1983, pp. 629–630.

U.S. Pat. No. 3,875,008 to Yoshino, et al describes the encapsulation of enzymes and/or microorganisms in the lumen of a hollow semi-permeable polymeric filament which may be opened or closed at its ends.

The hollow fiber permselective membranes have the disadvantages of requiring headers which are difficult to manufacture and seal, frequent breakage, and especially for the organic fibers, inherently slow separation rates due to the requirement of having to use relatively thick separation membranes to obtain the necessary strength required to support the weight of the membranes. Moreover, the hollow fiber cell culture devices generally function primarily as supports and merely adhere the cells or other biocatalysts to the outer surface of the hollow fiber or in the pores of spongelike hollow-fibers or in the pores of solid porous microspheres or microbeads, and therefor do not provide a sufficiently sterile environment.

The hollow semipermeable organic microcapsules and gelatinous microbeads and the hollow semipermeable fibers which encapsulate cells, bacteria or other biocatalysts can provide an adequate sterile environment but suffer from the defect of inherently slow permeation rates due to the wall thickness of the membrane. However, even where the biocatalyst is encapsulated within the lumen of a hollow fiber, as in the above mentioned Yoshino, et al patent, there is still the risk of fiber breakage which can contaminate and render useless the entire or substantial portion of a production run. In addition, to date no practical economical method has been developed to fabricate the hollow microcapsule containers with uniform size or wall thickness and therefore control of the biotech processes using bioreactors based on these hollow permselective microcapsules is extremely difficult. Still further, these organic microcapsules and gels are generally fragile and cannot be stacked to any significant height, or used in, for example, a fluidized bed process, since the weight of the column or particle-to-particle or particle-to-wall contact can rupture, distort, or otherwise damage and ruin the microcapsule containers and gel beads.

OBJECTS OF THE INVENTION

Accordingly, it is an object of the invention to provide bioreactors from inexpensive, easily manufactured, reusable or discardable, uniformly sized, high strength, porous hollow microspheres.

It is another object of this invention to provide structural support to gel immobilized biocatalyst without significantly diminishing permeation rates of nutrients, gases, reaction substrates or other desired substances into and out of the gel by encapsulating the immobilized biocatalyst in high strength hollow uniformly sized porous microspheres.

Another object of the invention is to provide biocatalysts encapsulated within rigid thin walled hollow, porous microspheres, the walls of which are uniform in diameter, thickness, porosity, and interconnecting void distribution, and which walls contain at their outer surface, inner surface, and/or intermediate location, a permselective membrane having a predetermined molecular weight cut-off wherein the biocatalysts are protected from contamination or inactivation by high molecular weight substances by the permselective membrane which effectively separates the hollow interior of the microsphere from its external surroundings with respect to high molecular weight substances.

A more specific object of the invention is to provide novel bioreactors for biotech processes wherein the containers of the bioreactors are hollow porous microspheres as support for permselective membranes wherein substantially the entire structural strength of the bioreactor is provided by the walls of the microspheres such that the permselective membranes can be substantially thinner than in conventional permselective membrane bioreactors, that is, in which the structural support function is separated from the permselective membrane function.

It is also an object of this invention to provide a process for encapsulating biocatalyst substances within non-rupturable hollow porous thin walled microspheres.

A still further object of this invention is to provide biotech processes for manufacture, purification, separation, and identification of various chemical substances which use the novel bioreactors.

Yet another object of the invention is to provide more economical, easier to control biotech process using uniformly sized hollow porous non-rupturable microsphere supported permselective membrane encapsulated biocatalyst as bioreactor.

Still yet another object of the invention is to provide microsphere encapsulated biocatalyst bioreactors which can be used in fixed bed, fluidized bed, and other batch, continuous or semi-continuous biotech processes.

These and other objects of the invention will become apparent as the description proceeds.

SUMMARY OF THE INVENTION

In one aspect, the present invention provides novel bioreactors which include, as the containers for containing and protecting the biocatalyst, hollow porous microspheres of substantially uniform diameter and substantially uniform wall thickness and porosity, and high mechanical strength, the porous wall or shell of the hollow microsphere including entrance means through which biocatalyst is introduced into the hollow interior or core of the microsphere, biocatalyst in the hollow interior of the microsphere, and fluid permeable means for immobilizing the biocatalyst within the hollow interior.

In one embodiment of the invention, the fluid permeable immobilizing means can be a reversible or irreversible gel. Where the biocatalyst is a living microorganism, the immobilizing means preferably includes a continuous, semicontinuous or discontinuous permselective membrane sealing the pores and the entrance means in the wall of the microsphere, such that the biocatalyst contained within the microsphere is prevented from escaping from the microsphere through the pores and entrance means, while only specific liquids, gases and/or organic molecules of predetermined molecular size, which is smaller than the size of the biocatalyst, can enter or leave the microsphere through the permselective membrane. The permselective membrane sealed microsphere containers can be used with any biocatalyst, such as enzymes, however, they are especially preferred when the biocatalysts are living viable microorganisms, including single cells, bacteria, viruses, fungi, molds, and yeast, both naturally occurring and modified, fused or genetically engineered.

In another aspect, the invention provides a process for producing the bioreactors from the hollow porous microspheres. According to this process, hollow porous microspheres each having entrance means in its porous wall or shell which is large enough for the biocatalyst to pass through into the hollow interior, are suspended in an inert or nutrient containing liquid medium, in which liquid medium the biocatalyst and a gel-forming reactant is dissolved or suspended, and sufficient pressure is applied to the resulting suspension to cause the dissolved or suspended biocatalyst and gel-forming reactant and the liquid medium to pass through the entrance means of the microsphere into the hollow interior of the microsphere.

In one embodiment of the process, the biocatalyst-gel forming reactant—filled microspheres are recovered from the suspending medium and placed in a second medium which causes the gel forming reactant to gellify, at least in the pores and entrance means whereby the resulting gel, as supported by the microsphere wall, encapsulates the biocatalyst within the intracapsular volume of the microsphere to thereby provide the fluid permeable immobilizing means.

In the embodiment of the invention wherein the fluid permeable immobilizing means is comprised of a semipermeable membrane material the gel immobilized biocatalyst filled microspheres are further treated with a membrane forming material whereby the previously formed gel in the entrance means and pores functions as a substrate on which the membrane is deposited by mechanical, chemical or mixed mechanical-chemical means. According to this embodiment, after recovery of the gel immobilized biocatalyst-filled microspheres, the biocatalyst-filled microspheres are contacted with a solution or suspension of the material forming the permselective membrane under conditions which will cause the membrane material to deposit on and/or react with the gel to fill, coat, seal, impregnate or otherwise close-off the entrance means and substantially all of the pores of the microspheres, thereby preventing the biocatalyst from escaping from the interior of the hollow microspheres while permitting diffusion of substances, such as nutrients, reactants, by-products, and the like, of predetermined molecular size through the permselective membrane into or out from the interior of the biocatalyst-filled microspheres. The gel may optionally be reliquefied to facilitate the activity of the biocatalyst. Where necessary, as might be the case, for example, with polymeric permselective membranes deposited from a solution of the polymer, the coated microspheres are recovered and the solvent is removed under sufficiently mild conditions to avoid inactivating the biocatalyst.

According to still another aspect of this invention an improved method for the biochemical production, purification or separation of useful substances or the identification and/or quantification of one or more substances in a mixture is provided in which the improvement involves the use of the novel bioreactors as described above. The bioreactors are maintained in an environment conducive to the production, purification, separation, identification and/or quantification of the desired substance but without degradation of the biocatalyst. In the case of chemically active biological materials, such as enzymes, hormones, antibodies and the like, the biocatalyst-filled microspheres are maintained in contact with a medium containing at least one low molecular weight material which is reactive with the biocatalyst and which reactive material(s) can diffuse through the gel or permselective membrane fluid permeable immobilizing means to react with the encapsulated biocatalyst. Depending on the molecular size of the desired end product, the end product can be recovered from the medium external to the microspheres or the microspheres with the encapsulated high molecular weight end product can be mechanically or chemically opened or the gel or permselective membrane can be dissolved or disrupted outside the reaction system to recover, detect and/or quantify the end product.

In the preferred embodiment of the invention in which the biocatalysts are in the form of living microorganisms, such as single cells, cell tissues, bacteria, viruses, yeast cells, and the like, and wherein a semipermeable membrane is used as the fluid permeable immobilizing means, the biocatalyst-filled microspheres are maintained in contact with a nutrient medium for the particular organism under culture conditions in which the organisms will generate the desired useful end product, usually an amino acid, nucleic acid, nucleotide, phosphatide, sugar, protein, glycoprotein, etc. Any nutrients necessary for maintenance and/or growth of the cells or other microorganisms but which have a molecular weight too large to pass through the permselective membrane will be included within the microsphere prior to formation of the permselective membrane. Where the end product is excreted from the microorganism and is of sufficiently small molecular size so that it can diffuse through the permselective membrane, the end product can be recovered from the external liquid nutrient medium. Where the end product is merely accumulated in the organism, as is the case, for example, with certain bacterial and yeast produced amino acids, proteins, etc., or where the molecular size of the end product is too large to diffuse out of the microspheres, the microspheres are withdawn from the nutrient medium and the end product is recovered by rupturing the walls of the microspheres or by removing, e.g. dissolving, the permselective membrane. In the latter case, the bioreactors can be recycled after replacing the permselective membrane and, if necessary, introducing fresh biocatalyst.

The invention will now be described in greater detail by specific embodiments and examples and with the aid of the accompanying drawings in which:

DETAILED DESCRIPTION OF THE INVENTION AND PREFERRED EMBODIMENTS

Hollow Porous Inorganic Microspheres

Figure 1:
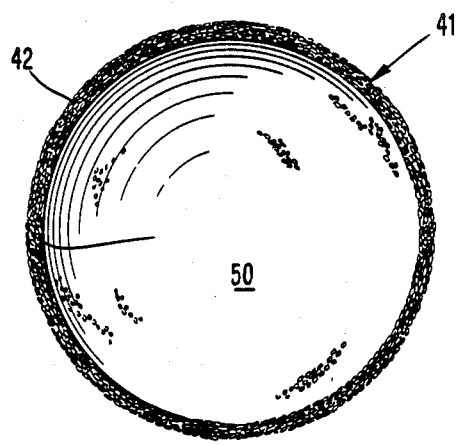
FIG. 1 is an enlarged cross-sectional view of a microsphere container according to the invention.

The hollow porous inorganic microspheres provide the uniformly sized containers for the biocatalyst and the structural support for the permselective membrane. Suitable methods for manufacturing these microspheres and their physical properties and dimensions are disclosed in and are the subject matter of applicant's copending application Ser. No. 639,126 "Hollow Porous Microspheres And Method And Apparatus For Producing Them" filed on Aug. 9, 1984. The entire disclosure of the copending application is incorporated herein in its entirety by reference thereto.

Quite briefly, the hollow porous microspheres are made from aqueous or non-aqueous suspensions or dispersions of finely divided inorganic or organic solid particles, particularly ceramic, glass, metal and metal glass particles, having particle diameters in the range of from about 0.01 to 10 microns ($\mu$), a binder material, a film stabilizing agent, a dispersing agent for the solid particles, and a continuous aqueous or non-aqueous liquid phase. The suspension or dispersion is blown into microspheres using a coaxial blowing nozzle, the microspheres are heated to evaporate the solvent and further heated or cooled to harden the microspheres. The hardened microspheres are then subjected to elevated temperatures to decompose and remove the binder and any residual solvent or low boiling or melting materials. The resulting porous hollow microspheres are then fired at further elevated temperatures to cause the particles to sinter and/or fuse at the points of contact of the particles with each other such that the particles coalesce to form a strong rigid network (lattice structure) of the sintered-together particles.

The application Ser. No. 639,126 discloses a method and apparatus for using a coaxial blowing nozzle and a blowing gas to blow hollow microspheres from a continuous liquid phase and dispersed particle film foming composition comprising feeding the blowing gas to an inner coaxial nozzle, feeding the dispersed particle film forming composition to an outer coaxial nozzle, forming spherically shaped hollow microspheres in the region of the orifice of the coaxial blowing nozzle and removing the hollow microspheres from the region of the orifice of the coaxial blowing nozzle. An embodiment of the method and apparatus is to use a transverse jet entraining fluid to assist in the microsphere formation and the detching of the hollow microspheres from the blowing nozzle. The continuous liquid phase of the dispersed particle film forming composition allows the hollow microspheres to be blown by forming a stable film to contain the blowing gas while the hollow microsphere is being blown and formed. The dispersed particles in the dispersed particle composition, as the dispersed particle composition is forming the hollow microsphere and after the microsphere is formed, link up with each other to form a rigid or relatively rigid lattice work of dispersed particles which dispersed particle lattice work with the binder and continuous liquid phase comprise the hollow green microspheres. The hollow microspheres after they are formed can be hardened in ambient atmosphere or by heating and removing a portion of the continuous phase. The hardened hollow green microspheres have sufficient strength for handling and further treatment without significant breaking or deforming of the microspheres.

The hardened green microspheres are treated at elevated temperatures to remove the remainder of the continuous liquid phase and volatile materials such as binder, film stabilizing agent and dispersing agent. The treatment at elevated temperatures sinters and coalesces the dispersed solid particles to form rigid hollow porous microspheres that are substantially spherical in shape, have substantially uniform diameters and have substantially uniform wall thickness. The heating at elavated temperatures, in removing the continuous phase and added materials, creates interconnecting voids in the walls of the microspheres which result in the porous characteristics of the microspheres. The sintering and coalescing of the dispersed solid particles, depending on the time and temperature of the heating step can cause a small degree of compaction of the dispersed particles and can cause the coalescing of the particles at the points in which they are in contact to form rigid, uniform size and shaped microspheres of uniform wall thickness, uniform void content and uniform distribution of voids in the walls and high strength. Because the porosity is a result of the removal of the continuous phase from uniformally dispersed solid particles, the pores are continuous from the outer wall surface of the microsphere to the inner wall surface of the microsphere and the walls of the microspheres have substantially uniform void content and uniform distribution of the voids that are created.

The hollow porous microspheres preferably are substantially spherical, have substantially uniform diameters, and have substantially uniform wall thickness and the walls have uniform void content and void distribution and voids which are connected to each other and to the inner and outer microphere wall surfaces. The walls of the hollow porous microspheres are free of latent solid or liquid blowing gas materials, and are substantially free of relatively thinned wall portions or sections and bubbles.

The hollow green microspheres and hollow porous microspheres made in accordance with method and apparatus of application Ser. No. 639,126 can be made from a wide variety of film forming dispersed particle compositions, particularly dispersed ceramic, glass, metal, metal glass and plastic particle compositions and mixtures thereof. The dispersed particle compositions comprise an aqueous or nonaqueous continous liquid phase and have the necessary viscosities when being blown to form stable films. The hollow microsphere stable film wall after the microsphere is formed rapidly changes from liquid to solid to form hollow green microspheres. The hollow green microspheres can be substantially spherical in shape and can be substantially uniform in diameter and wall thickness.

The hollow green microspheres as they are being formed and/or after they are formed can have a portion of the continuous liquid phase removed from the dispersed particle composition from which the microspheres were formed. The removal of continuous liquid phase can act to bring the dispersed particles closer together and into point to point contact with each other. The dispersed particles can then link up with each other to form a rigid or relatively rigid lattice work of dispersed particles which particles lattice work with the binder (if one is used) and continuous liquid phase (that remains) comprise the hollow green microspheres. The hollow green microspheres are free of any latent solid or liquid blowing gas materials or latent blowing gases. The walls of the hollow green microsphers are free or substantially free of any holes, relatively thinned wall portions or sections, trapped gas bubbles, or sufficient amounts of dissolved gases to form bubbles. The term "latent" as applied to latent solid or liquid blowing gas materials or latent blowing gases is a recognized term of art. The term latent in this context refers to blowing agents that are present in or added to glass, metal and plastic particles. In the prior art processes the glass, metal and plastic particles containing the "latent blowing agent" are subsequently heated to vaporize and/or expand the latent blowing agent to blow or "puff" the glass, metal or plastic particles to form microspheres. The hollow green microspheres, because the walls are substantially free of any holes, thinned sections, trapped gas bubbles, and/or sufficient amounts of dissolved gases to form trapped bubbles, are substantially stronger than the hollow green microspheres heretofore produced. The hollow green and hollow porous microspheres contain a single central cavity, i.e. the single cavity is free of multiple wall or cellular structures. The walls of the hollow green and hollow porous microspheres are free of bubbles, e.g. foam sections.

The hollow green and hollow porous microspheres can be made in various diameters and wall thickness, depending upon the desired end use of the microspheres. The microspheres can have an outer diameter of 200 to 10,000 microns, preferably 500 to 6000 microns and more preferably 1000 to 4000 microns. The micropsheres can have a wall thickness of 1.0 to 1000 microns, preferably 5.0 to 400 microns and more preferably 10 to 100 microns. When the dispersed particles are sintered, the smaller particles can be dissolved into the larger particles. The sintered particles in the hollow porous microspheres can be generally regular in shape and have a size of 0.1 to 60 microns, preferably 0.5 to 20 microns, and more preferably 1 to 10 microns.

In certain embodiments of the invention, the ratio of the diameter to the wall thickness, and the conditions of firing and sintering the hollow microspheres can be selected such that the microspheres are flexible, i.e., can be deformed a slight degree under pressure without breaking. The preferred embodiment of the invention, particularly with the ceramic materials, is to select the ratio of the diameter to wall thicknes and the conditions of firing and sintering the hollow porous microspheres such that rigid hollow porous microspheres are obtained.

The hollow microspheres produced using the transverse jet embodiment are substantially spherical and have substantially uniform diameters and wall thickness. The hollow microspheres that are produced without the use of an external fluctuating pressure field, e.g., without the use of the transverse jet entraining fluid, can be substantially spherical and can have substantially uniform diameters or they can have thickened wall portions on opposite sides of the microspheres at the points at which the filaments are connected. The thickness of the thickened portions depends in part on the viscosity of the dispersed particle composition, the rate of hardening, the distance away from the coaxial blowing nozzle when they harden and the ability of the surface tension properties of the dispersed particle composition to absorb and distribute in the wall of the microsphere the portions of the dispersed particle composition that form the filaments.

The preferred hollow microspheres are the substantially spherical microspheres. However, in some applications the hollow microspheres with the thickened wall portions can also be used. The thickened wall portions can be 1.01 to 2.0 times the microsphere wall thickness; can be 1.1 to 1.5 times the microsphere wall thickness; and can be 1.2 to 1.3 times the microsphere wall thickness. The cross section of the microsphere other than the thickened wall portion section is substantially spherical and of substantially uniform wall thickness. All the microspheres produced under a given set of operating conditions and dispersed particle composition constituents are substantially the same in sphericity, wall thickness, void content and void distribution. A specific advantage of the process of the present invention is that in the production of hollow micropheres, the preceeding and the following microspheres that are produced are substantially the same. The lower viscosity dispersed particle compositions tend to produce the more spherical microspheres and the higher viscosity dispersed particle compositions tend to produce microspheres with thickened wall portions at opposite ends of the hollow microspheres.

Without intending to be limiting but rather to be used as a point of reference the following Table I provides exemplary relationships between the outer diameters of the microspheres, microsphere wall thickness, dispersed particle size, and ratio of the microsphere wall thickness to the outside diameter of the microsphere.

TABLE I

|  | Broad | Preferred | More Preferred |
|---|---|---|---|
| Diameter (microns) | 200 to 10000 | 500 to 6000 | 1000 to 4000 |
| Wall thickness (microns) | 1.0 to 1000 | 5.0 to 400 | 10 to 100 |
| Dispersed particles (microns) | 0.005 to 60 | 0.05 to 20 | 0.1 to 10 |
| Macro particles | 1.0 to 1000 | 5.0 to 400 | 10 to 100 |

TABLE I-continued

|  | Broad | Preferred | More Preferred |
|---|---|---|---|
| (microns) |  |  |  |
| Ratio of wall thickness to outside microsphere diameter | 1:4 to 1:500 | 1:10 to 1:300 | 1:20 to 1:200 |

In certain embodiements of the invention, for example, where the hollow microspheres are used as catalyst supports or to contain catalyst,in biotech processes, the hollow microspheres can have the dimensions shown in the following Table II.

TABLE II

|  | Preferred | More Preferred |
|---|---|---|
| Diameter (microns) | 1200 to 6000 | 2000 to 4000 |
| Wall thickness (microns) | 10 to 200 | 20 to 100 |
| Dispersed particles (microns) | 0.05 to 10 | 0.1 to 5 |
| Macro particles (microns) | 10. to 200 | 20 to 100 |
| Ratio of wall thickness to outside microsphere diameter | 1:10 to 1:300 | 1:50 to 1:200 |
| Dispersed particles (Vol. %) | 20 to 70 | 40 to 60 |
| Macro particles (Vol. % dispersed particles) | 1 to 10 | 2 to 6 |

The macro particle size is selected to be about the same or slightly larger in size than the thickness of the wall of the microsphere in which it is to create uniform size macro pores. Thus in microspheres having wall thickness of for example 10 to 200 microns, the macro particles would be about 10 to 200 microns in size, e.g., slightly larger than the wall thickness. The diameter of the macro pore can of course be made larger than the thickness of the microsphere wall if such is desired.

The macro particles can be about 0.8 to 4.0 times the thickness of the microsphere wall, preferably the macro particles are 1.1 to 2.0 times the thickness of the microsphere wall, and more preferably the macro particles are 1.1 to 1.5 times the thicknes of the microsphere wall. Where the macro particles are smaller, e.g. 0.8 times the wall thickness, when fired at elevated tempertures, the vaporization of the macro particles blows through the wall.

This embodiment allows the creation in the microsphere wall of macro pores of a predetermined size such that materials, such as living microorganisms that are of a size of, for example, 5 to 100 microns, can be given an access path into the interior of the microsphere without injury to the living microorganisms.

In an embodiment of the invention in which the hollow porous microspheres have a diameter of 1200 to 6000 microns and a wall thickness of 10 to 200 microns, the use of macro particles of 10 to 200 microns obtains substantially uniform size macro pores of 10 to 200 microns.

Hollow porous microspheres produced by the process of application Ser. No. 639,126 can be 200 to 10,000 microns in diameter and can have 1.0 to 1000 microns wall thickness. The walls of the hollow microspheres comprise particles sintered together at the points of contact of the particles. The sintered together particles form the walls of the hollow micropsheres and define within the walls interconnecting voids. The walls of the microspheres have substantially uniform void content and the interconnecting voids are continuous and extend from the outer wall surface to the inner wall surface of the hollow microspheres and the interconnecting voids are substantially uniformly distributed in the walls of the hollow microspheres. The walls of said hollow microspheres are free of latent solid or liquid blowing gas materials and are substantially free of relatively thinned wall portions or sections and bubbles.

The hollow porous microsphere containers of this invention, in addition to their uniformity in structure, have the highly advantageous characteristic of high mechanical strength due to the sintering together of the solid dispersed wall-forming particles. Due to this high mechanical strength, the microsphere containers are non-rupturable under the conditions of actual use in biotech processes. Thus, as used herein, and in the appended claims, "non-rupturable" means the ability to withstand the forces exerted by contact with other microspheres or the walls and surfaces of the biotech apparatus, as well as hydrostatic forces and pressures encountered in biotech processes, including fluidized bed, stacked bed, plug flow, and other types of biotech processes, without any significant deformation of shape and without breakage and, further, without imparting stress forces on the permselective membrane or other fluid permeable immobilizing means. Preferably the walls of the hollow porous microsphere containers are rigid and are capable of withstanding two point contact pressure of at least 30 psi (2.1 kg/cm$^2$), preferably from about 50 psi (35 kg/cm$^2$) to about 300 psi (21.1 kg/cm$^2$) and hydrostatic pressure of at least 150 psi (10.5 kg/cm$^2$), preferably from about 150 psi (10.5 kg/cm$^2$) to about 1500 psi (105.7 kg/cm$^2$). As used herein "two point contact pressure" is measured with respect to a one-inch square tightly packed monolayer of the microspheres resting on a hard flat surface with a flat mass placed thereon. The weight of the mass causing breakage of one or more microspheres divided by one square inch is the "two point contact pressure."

Figure 5:
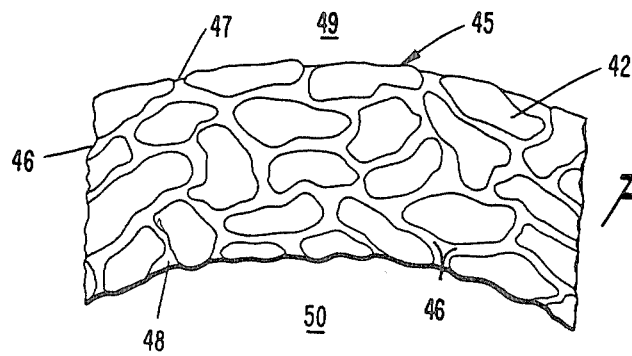
FIG. 5 is an exploded schematic view of a segment of the microsphere wall of FIG. 1.
Figure 6:
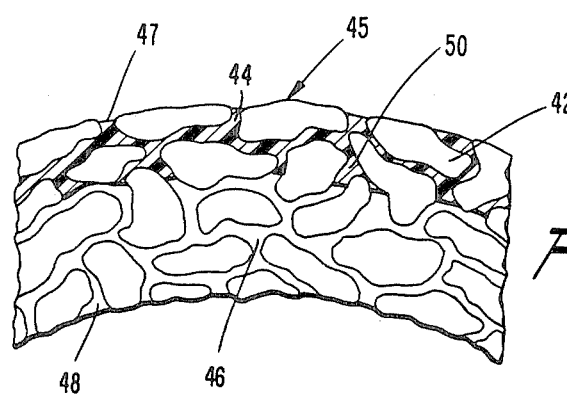
FIG. 6 is an exploded view of a section of the microsphere wall of FIG. 4 including the permselective membrane.

As can be seen from FIGS. 1 and 5, the sintered-together particles 42 forming the solid porous wall 45 of the microsphere 41 define, within the wall, interconnecting voids or channels 46. For simplicity of illustration, the particle-to-particle contact of the sintered together particles is not shown. These interconnecting voids are continuous and extend, often in tortuous or curved, but smooth paths, from the surface pore or opening 47 at the outer wall surface to the surface pore or opening 48 at the inner wall surface, thereby providing generally tortuous, but smooth, i.e. without excessively sharp bends or curves, paths or passageways for transporting gases, liquids and low molecular weight solutes and very finely divided, e.g. submicron, dispersed solid materials, from between the exterior (referred to as "extracapsular" space) 49 to the single hollow central void, i.e. interior (referred to as "intracapsular" space) 50 of the hollow microsphere. The interconnecting voids are substantially uniformly distributed in the walls of the hollow microspheres (referred to as "uniform void distribution") while the microspheres, because of the unique production process, also have a substantially uniform porosity (also referred to as "void content") and diameter and wall thickness from microsphere to microsphere.

Generally, the microspheres will have an outer diameter of about 200 to 10,000 microns, preferably about 1200 to 6000 microns, and more preferably about 2000 to 4000 microns and a wall thickness of about 1 to 1000 microns, preferably 10 to 200 microns and more preferably 20 to 100 microns. The ratio of the wall thickness to outer diameter can be in the range of from about 1:4 to 1:500, preferably 1:10 to 1:300, and more preferably 1:50 to 1:200. The porosity of the walls is generally from about 5 to 45%, preferably 15 to 35%, and more preferably 25 to 30% by volume of the microsphere wall. The interconnecting voids or channels will, depending on the size of the dispersed particles and the particle size distribution of the dispersed particles and the porosity of the microsphere walls, range from about 0.05 to 8 microns, generally from about 0.1 to 5 microns, and more generally from about 0.1 to 3 microns.

For most non-living biocatalysts, e.g. enzymes, antibodies, lymphokines, etc., having molecular weights of less than about 100,000 to 200,000 daltons, the pore sizes or at least a substantial portion of the pores, will be sufficiently large to permit free passageway of these biocatalysts from the extracapsular space into the intracapsular space (the hollow core) of each microsphere.

Figure 3:
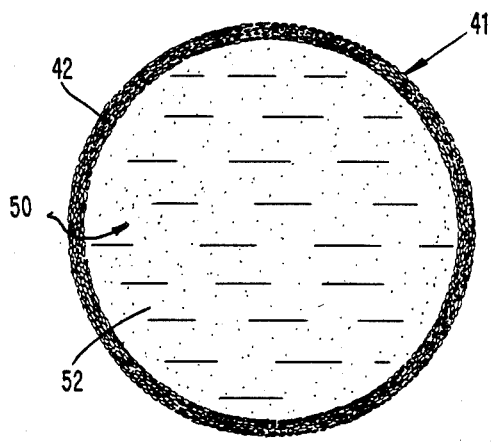
FIG. 3 is similar to FIG. 1 but showing the intracapsular space of the microsphere filled with a solution or suspension of biocatalyst, such as an enzyme.

Thus, as illustrated in FIG. 3, enzymes 52 dispersed in liquid medium 51 fill the intracapsular space 50 through the channels 46 between the sintered together solid particles 42.

Figure 2:
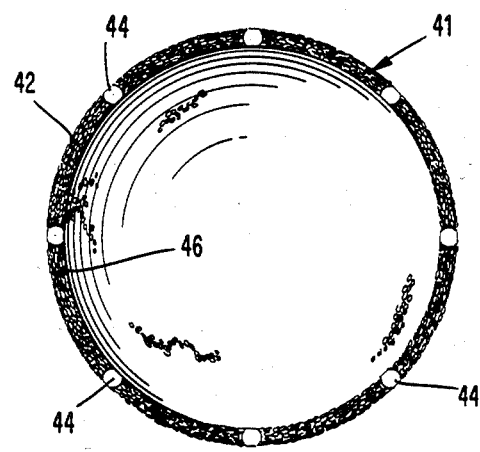
FIG. 2 is an enlarged cross-sectional view of a modified embodiment of the microsphere container including a multiplicity of macropores extending through the microsphere wall.
Figure 4:
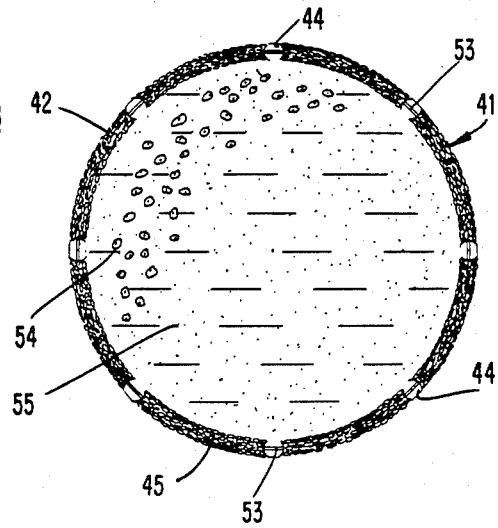
FIG. 4 is similar to FIG. 2 but showing the intracapsular space of the microsphere filled with a suspension of cellular biocatalyst and further showing a permselective membrane.

However, the pore size may be smaller than or only slightly larger (e.g. up to about 100% larger) than the maximum dimension of the biocatalyst - this will generally be the case for cells, tissues, bacteria, yeast cells, and other microorganisms. In such a case, the microspheres illustrated in FIGS. 2 and 4 can be used. As seen in FIGS. 2 and 4 at least one, and preferably about 5 or more entrance means 44, e.g. openings or passageways, of larger dimensions than the largest pore diameter, are provided to ensure that the cellular biocatalyst 54 suspended in broth 55 will be able to pass through the entrance means 44 which extend through the wall 45 of the microsphere 41 into the intracapsular space 50 of the microsphere prior to the depositing or formation of the gel or permselective membrane immobilizing means 44. The relatively large entrance means in the walls of the microspheres, e.g. which are at least twice as large as the maximum pore size, are referred to herein as "bioports" or "macropores." However, it is understood that the term "entrance means" as used herein, and in the appended claims, can also include the pores and interconnecting voids in those cases where the biocatalyst dimensions are substantially smaller, e.g. 50% or less, than the dimensions of the pores and interconnecting voids and can, therefore, freely pass from the extracapsular space to the intracapsular space. Preferably, however, even with the smaller dimensioned biocatalysts, it is preferred to include one or more macropores 44 in the microsphere walls to facilitate and expedite the process of filling the microspheres with biocatalyst and subsequently removing the biocatalyst.

As described in the copending application Ser. No. 639,126, the macropores can be obtained by incorporating in the solid particle suspension or dispersion, prior to the blowing step, a small percentage of decomposable particles (macroparticles) having a diameter greater than the maximum dimension of the biocatalyst, for example, about 1 to 1000μ, preferably 5 to 200μ, more preferably about 10 to 200μ, especially preferably about 20 to 100μ. These decomposable macroparticles are entrapped along with the smaller dispersed solid particles in the wall or shell of the microsphere. However, the decomposable macroparticles are decomposed at the step of decomposing the organic binder or at the subsequent step of sintering the dispersed particles depending on the decomposition temperature of the decomposable macroparticles leaving behind large openings (macropores), such as shown in FIG. 2.

Figure 7:
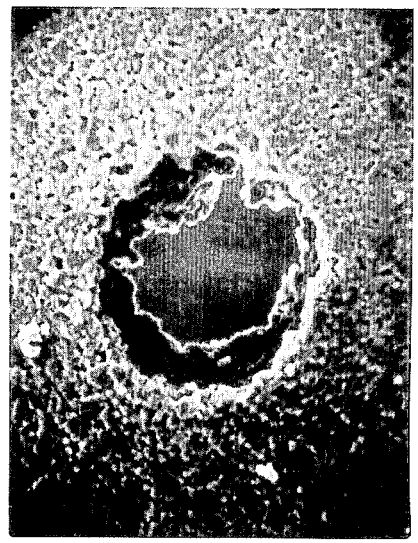
FIG. 7 is a microphotograph (900×) of a section of a microsphere wall showing a macropore therein.

FIG. 7 is a microphotograph (900× magnification) showing a section of a microsphere wall (40 micron thick) after decomposition of acrylic macroparticles of about 50μ diameter. The sintered solid particles forming the walls are alumina ($Al_2O_3$) particles having a particle size in the range of about 1 to 3 microns. The microsphere is about 4000 microns in diameter.

Examples of materials from which the decomposable macroparticles can be formed include, for example, carbon, naphthalene, anthracene, camphor, polyformaldehyde resins, polyethylene, polypropylene, nylon, and, more generally, any of the thermoplastic or thermosetting organic resins or polymers which can be used as the binder, provided however that the decomposable macroparticles are not soluble in and do not swell or substantially swell in the solvent for the binder. In addition, metal and glass beads or pellets having a melting temperature below the sintering temperature, preferably at least 100° C. below the sintering temperature can also be used.

As can be seen from the microphotograph of FIG. 7, the perimeter of the macropore is generally free of sharp or jagged protrusions which could result from extension into the macropore of portions of one or more of the finely divided solid wall-forming particles since any such sharp or jagged protruding solid particles will tend to be smoothened by the subsequent sintering step. However, it is possible to even further smoothen the surface of the macropore by using as the macroparticles a material, such as glass and metals, which at least partially soften and melt, rather than decompose, at the operating temperature. In such case, when the microsphere is heated, at least a portion of the macroparticle will diffuse and penetrate into and between the dispersed solid particles surrounding and coating the macroparticle thereby assuring leaving behind a smooth macropore surface (periphery). Furthermore, it is possible to select mutually reactive materials for the finely divided solid particles and the macroparticles, for example, alumina solid particles and glass macroparticles, which will react to form alumina silicate, at or below the sintering temperature, thereby further strengthening, as well as smoothening, the macropore surface.

The amount of the decomposable particles incorporated in the suspension or dispersion is not particularly critical insofar as the amount is sufficiently high so that all of the formed porous hollow microspheres contain at least one, preferably at least 5, and especially preferably at least about 10 to 20 decomposable particles in their walls. On the other hand, the amount of decomposable particles should not be so high that the blowing operation is impeded or that the mechanical strength of the microsphere wall is weakened. Generally, the amount of the decomposable particles will range from about 1 to 10%, preferably from about 2 to 6%, especially preferably from about 2 to 4%, by volume of the total volume of dispersed solid particles, to satisfy the above requirements.

Generally, the material of the dispersed solid particles forming the walls of the microspheres is not particularly critical, so long as it is compatible with and nontoxic to the biocatalyst and inert to the biotech process, and any of the ceramic particles, glass particles, metal particles, metal glass particles, and plastic particles disclosed in the aforementioned patent application Ser. No. 639,126 can be used.

On the other hand, it is often preferred or necessary in certain biotech processes for the biocatalyst to adhere to a substrate (in the case of the present invention, the substrate being the inner wall surface of the hollow microsphere, as well as the portions of the semipermeable membrane exposed to the intracapsular space). For example, as is well known in the art, mammalian cells are generally anchorage dependent for growth (cell division). Also, it is often preferred to immobilize or fix enzymes to substrates in biotech processes. In such cases, therefore, the material of the dispersed particles will be selected based on its ability to provide a surface to which the biocatalyst can adhere by physical and/or chemical bonding. Most materials will naturally meet this requirement, although to differing degrees. Furthermore, it is also known in the art to provide chemical treatment to substrates to increase their ability to bond to specific biocatalysts.

It is preferred that, for reasons discussed herein, the wall forming material, i.e. solid particles, should be inorganic rather than organic.

An inorganic material has a variety of marked advantages. The first is that microbes do not readily attack inorganic materials since their nutrient requirements are primarily focused to carbon and nitrogen containing materials. Organic substances, such as carbohydrates, proteins, etc., are readily attacked not only by the microbes but also by the extracellular enzymes that are elaborated by the organism. As the organic particles are destroyed, the accumulation of microbes is reduced. In addition to durability, the inorganic microspheres have the advantage of dimensional stability and mechanical strength when contrasted to organic microspheres. By retaining the pore morphology under a variety of pressure and flow conditions, the microsphere is protected from deformation. Again, this is an advantage in terms of product formation biomass accumulation and/or process control.

An additional advantage of an inorganic microsphere is its relatively high density. Most organic materials have densities in the neighborhood of 1.0 or less while most of the inorganic materials have densities greater than 2.0. Under these circumstances, inorganic material microspheres having desired bulk densities approximating that of the aqueous nutrient culture broth or other liquid system can be more easily obtained.

On the other hand, as compared to the known solid porous microbead carriers used as biocatalyst supports, the hollow porous microspheres according to this invention have significantly lower densities. These low densities (or mass) provide the following highly important advantages: less mechanical energy is required to mix or stir suspensions of the microsphere bioreactors in biotech processes thereby providing lower overall costs for carrying out the process. The lower bioreactor mass reduces the impact forces or collision pressures of particle-to-particle, i.e. microsphere-to-microsphere, collisions, thereby reducing the likelihood of damage to the microsphere walls and more importantly, due to the inherent strength of the microsphere walls, reducing the likelihood of damage or shearing stresses to the permselective membrane or other fluid permeable immobilizing means. As is generally known in the art, stresses applied to permselective membranes can alter the molecular weight cut-off point of the membrane and thereby make control of the biotech process more difficult.

Mixtures of two or more materials forming the dispersed particles can also be used, provided, however, that the different composition particles can be sintered to each other without melting or fusing the particles to such an extent as to substantially decrease the porosity of the microsphere to below about 5%, preferably 15%.

Biocatalysts

Any chemically active biological substance or living cells or microorganism can be used as the biocatalyst which is to be encapsulated within and protected by the hollow porous microspheres.

As examples of chemically active biological substances mention can be made, for example, of enzymes, such as carbonic anhydrase, urease, asparginase, lactate dehydrogenase (LDH), glutamate oxaloacetate transaminase (GOT), aminoacylase, aspartase, esterase, fumarase, glucose isomerase, lactase, penicillin acylase, racemase, steroid dehydrogenase, etc., hormones, antibodies, hemoglobin, interferons, lymphokines, such as interleukin-1 and interleukin-2, macrophage activating factor (MAF), colony stimulating factor (CSF), etc., and other chemically active materials including, for example, ion exchange resins and activated charcoal. In place of cell-free enzymes, ruptured cells or whole cells which produce the desired enzymes can also be used. Mixtures of biocatalysts can also be used.

In addition to the aforementioned examples of non-living biocatalyst materials, there are many biotech processes which utilize living substances. As examples of living biocatalysts mention can be made of individual cells, cellular masses, tissues and organelles, and microbes or microorganisms including yeast, bacteria, viruses, fungi, mold and algae. Bacteria and yeast are the preferred microbes.

The cellular biocatalysts include, for example, animal cells, especially mammalian cells, including bovine, porcine, ovine, monkey and human cells, mouse, and hamster cells; plant cells; and cell masses, fused cells, e.g. hybridoma cells, and cell tissues from any of these types of cells. Both normal cells and tumor cells as well as genetically engineered cells and cells modified by conjugation, hybrid DNA, or fusion can be used. Cell types which are adapted to grow in suspension culture, as well as anchorage-dependent cells can be encapsulated in this invention. Specific examples include mammalian islets of Langerhans, fibroblasts, leukocytes, lymphoblastoids, pancreatic beta cells, alpha cells, delta cells, various ratios thereof, bovine and human anterior pituitary cells, chicken embryo, epithelium, rat liver, and established cell lines, such as Hela human cervix (carcinoma) cells, rhesus monkey kidney cells (LLC-MK$_2$), Syrian baby hamster kidney cells (BHK-21), etc. Of course, any other cells, tissues, cell lines, etc., capable of being maintained and/or grown in a suitable culture medium can be encapsulated in the hollow microspheres according to this invention.

Any of the viruses which can be cultivated by cell culture techniques in encapsulated form, such as Rauscher murine leukemia virus, hepatitis A virus, etc., can be used in this invention. To cultivate the viruses they are first inoculated in individual cells according to known principles and the inoculated cells are then encapsulated in the hollow microspheres.

Similarly, any type of bacteria or yeast microbes which can be cultivated in a suitable culture medium can be used. As non-limiting examples of suitable microbes mention can be made of, for example, cyan-utilizing microorganism, pencilin acylase producing microorganism, macrolide type antibiotic producing microorganism and the like.

As specific non-limiting examples of microorganisms, there can be mentioned *Streptococcus lactis, Saccharoinyces cerevisiae, Lactobaccillus delbrueckii, Aspergillus niger,* Acetobacterrances, *Bacterium curvum, Lactobacillus bulgaricus, Lactobacillus casei, Lactobacillus leichmannii, Citromyces pfefferianus, Penicillin arenarium, Rhizopus nigricans, Penicilin notatum, Streptomyces grisesus, Streptomyces citrovorus, Penicillin roqueforti, Lactobacillus cucumerus, Lactobacillus bifidus, Lectobacillus acidophilius, Escherichia coli, Saccharomyces cerevisiae, Saccharomyces anamensis, Aspergillus oryzae, Saccharomyces ellipsoideu, Saccharomyces pastorianus, Clostridium butyricum, Streptococcus lactis, Propionibacterium freudenreichii, Streptomyces rimosus forma paromycinus, Actinomyces griseus, Streptomyces kanamyceticus, Streptomyces humidus, Seratia marcescens, Bacillus subtilis,* and Rhodospirillum rubrum.

"Encapsulation" of Biocatalyst

The manner by which the biocatalyst is introduced into the hollow porous microsphere container is not particularly critical so long as the activity of the biocatalyst is not substantially diminished or destroyed in the process. Accordingly, by whatever technique is used, it will be necessary to maintain an environment which is conducive to the maintenance of the biological and/or chemical activity of the biocatalyst, for example, temperature, pH, and the like, as well, of course, as a suitable nutrient broth or culture liquid in the case of living cells and other microorganisms. The appropriate environmental conditions for any particular biocatalyst will be well known or readily ascertainable by the practitioner. Usually, because of the high temperatures to which the microspheres are subjected during sintering, e.g. about 500° C. or more, it may not necessary to sterilize the microspheres prior to encapsulating the biocatalyst. Of course, a sterile environment including all process equipment, should be maintained until at least after formation of the gel or permselective membrane.

Generally, it should be sufficient to merely suspend the microspheres in a liquid carrier medium in which the biocatalyst is dissolved, suspended or dispersed, and to allow the biocatalyst and liquid and any nutrients, or other substances added to the liquid carrier, to flow, or to diffuse by capillary action, through the entrance means or both the entrance means and pores in the walls of the porous hollow microspheres, depending on the size of the biocatalyst, into the intracapsular space. The suspension can be gently stirred by mechanical mixing, aerobic mixing or other gaseous mixing, to ensure homogeneity of the system and uniformity of the amount of biocatalyst in contact with individual microspheres. It is also preferred that the liquid carrier be capable of wetting the material forming the walls of the microsphere containers to assist in the filling process. Wetting agents which are inert to the biocatalyst can be added to the liquid carrier medium for this purpose.

The concentration of the biocatalyst in the liquid carrier and the amount of biocatalyst relative to the total volume or number of the microspheres will be selected depending on the nature and type of biocatalyst and the biotech process and on the internal volume of the microspheres and can be readily determined by the skilled practitioner.

While the driving force of capillary action can be sufficient to fill the hollow microspheres with the suspended, dispersed or dissolved biocatalyst, this technique requires especially long times, on the order of about several hours, to fill all of the microspheres, and may not be practical where the solid particles forming the microsphere walls and defining the interconnecting voids or pores and the entrance means are not sufficiently wetted by the liquid phase of the biocatalyst solution, suspension or dispersion, since the driving force of the capillary action may not be sufficient to overcome the atmospheric pressure within the intracapsular space.

Therefore, according to a preferred embodiment of the invention, the driving force for filling the hollow microspheres with the biocatalyst and liquid medium is increased by applying pressure to the system. The applied pressure can be fluid pressure, e.g. hydrostatic pressure, isostatic pressure, pneumatic pressure or dynamic pressure, e.g. centrifugal force. Preferably, the suspension of the microspheres in the liquid carrier-biocatalyst system is subjected to both fluid pressure and centrifugal force in a centrifuge apparatus.

Generally, the amount of the applied pressure will not be particularly critical insofar as the pressure is not so great as to rupture the walls of the microspheres or harm the biocatalyst and which will maintain laminar flow of the biocatalyst-liquid medium system. Pressures in the range of from about 3 psi to about 30 psi, preferably from about 5 psi to about 25 psi are satisfactory. Preferably, the pressure is increased gradually since abrupt pressure increases are more likely to be destructive to the microspheres and/or biocatalysts. It is usually sufficient to raise the pressure at a rate of from about 0.5 to about 3 psi/minute, preferably from about 1 to about 2 psi/minute. The pressure should be maintained until at least substantially all of the microspheres are filled with the biocatalyst and liquid medium. Generally, the time required to fill the microspheres will be inversely proportional to the applied pressure and directly proportional to the size and number of entrance means and pores in the walls of the microspheres which connect the extracapsular space to the intracapsular space. Times on the order of from about 30 seconds to about 60 minutes, generally from about 1 minute to about 40 minutes are satisfactory.

From an economical point of view, since no special apparatus is required one preferred filling method is to simply load a pressure vessel with the microspheres and thereafter to fill the closed pressure vessel with the biocatalyst-containing liquid medium under positive pressure using a suitable pressure pump.

Another relatively simple technique for filling the hollow microspheres is to "pull" the biocatalyst-liquid medium system into the microspheres through the entrance means and/or pores by forming a thin layer, preferably a single layer, of the microspheres on a microporous sheet or belt and applying a vacuum to the reverse side of the sheet or belt whereby the biocatalyst-liquid medium system will be sucked into the intracapsular spaces of the microspheres. If desired, a positive pressure can simultaneously be applied to the biocatalyst-liquid medium system.

When centrifugal force is used to assist in the filling of the microspheres, a suspension or dispersion of the microspheres in the biocatalyst-containing liquid medium is introduced into a centrifuge tube and rotated at a speed, which depending on the length of the arm carrying the centrifuge tube, will be sufficient to maintain the pressures discussed above. It is also generally preferred to partially fill the microspheres under fluid pressure prior to or during the application of centrifugal force to increase the density of the microspheres relative to the liquid medium.

The amount of the liquid medium to fill the microspheres can be easily calculated based on the volume of the hollow core of a microsphere multiplied by the total number of microspheres. Therefore, the total amount of liquid medium for the filling operation will generally be the volume to fill the microspheres, plus the volume to fill the vessel in which the microspheres are contained less the volume occupied by the microspheres (based on the outside diameter of a microsphere). In other words, assuming the external housing, e.g. pressure vessel, centrifuge tube or other container for the empty microspheres, is filled to capacity with the microspheres (generally about 55–70% of the total volume depending on packing density for a perfect sphere) then the liquid medium can occupy the void volume between individual microspheres plus the additional volume of the hollow cores of the microspheres (neglecting the volume occupied by the interconnecting voids in the walls of the microspheres). Therefore, by metering the amount of the liquid medium supplied to the external housing it can readily be determined when the microspheres are filled with the liquid medium. However, it is generally sufficient to use excess liquid medium and to carry out the filling operation for a period of about 20 to 60 minutes, preferably 30 to 40 minutes to assure adequate filling of the microspheres with the dissolved or suspended biocatalyst and liquid medium.

Furthermore, it is not essential to completely fill the microspheres with the biocatalyst and liquid medium and satisfactory results can be obtained when at least 70%, preferably at least 85%, of the total available volume of the microsphere is filled, the remaining at most 30%, preferably at most 15% of the total volume being filled with air, oxygen, or other gas which is not detrimental to, or is needed for, the biochemical process, such as, for example, oxygen-containing gas for culturing of mammalian cells and aerobic bacteria.

Biocatalyst Immobilization

After the microspheres are filled with the biocatalyst-containing liquid medium it is necessary to seal the entrance means and pores in the walls of the microspheres in order to immobilize the biocatalyst within the microspheres.

It is a feature of the present invention that since the microsphere wall, per se, provides all of the required rigidity and structural support for the bioreactor, it is not necessary for the immobilizing means to contribute to the mechanical stability and structural integrity of the bioreactor. Accordingly, it is sufficient to use any immobilizing means which will effectively retain the biocatalyst in the intracapsular space while permiting influx and outflow of gases, nutrients, reactants, by-products, etc., which are required for the biotech process and/or for the preservation, maintenance and/or growth of the biocatalyst.

Thus, in the case, for example, of enzymes, the immobilization may be effected simply by chemical bonding, for example, by aldehyde fixation, or any of the many other techniques known in the art.

A preferred means for immobilizing the biocatalyst within the microspheres is by encapsulation of the biocatalyst in a fluid permeable gel formed in situ in the microspheres. According to this embodiment of the invention, a gel-forming material or precursor is included in the liquid medium carrier for the biocatalyst and, after the microcapsules are filled as described above, the gel-forming material or precursor is activated to cause gellation. For example, a water-soluble gum can be used as the gel-forming material. After the microcapsules are filled, they can be separated from the liquid medium and transferred to a solution at gel-forming conditions, for example, temperature, pH, or ionic conditions. The techniques for formation of permanent and reversible fluid permeable gels is well known in the art and any of the conventional techniques can be used.

In an especially preferred embodiment of the invention, the biocatalyst is immobilized within the intracapsular space of the microspheres with a permselective membrane material which will retain the biocatalyst within the microsphere but which will allow gases, nutrients, reactants, wastes, and by-products to pass through or across the permselective membrane while preventing microorganisms, such as viruses and bacteria, which are, or may be, harmful to the biocatalyst, especially living cells or other microorganisms, or to the biological process, from entering the microsphere.

According to the preferred embodiment of the invention, the permselective membrane can be formed in situ within the entrance means and the pores of the microspheres, using well-known interfacial polymerization techniques, such as those disclosed, for example in U.S. Pat. Nos. 4,324,683, 4,322,311 and 4,251,387 to Lim and Moss, U.S. Pat. Nos. 4,352,883 or 4,391,909 to Lim, U.S. Pat. Nos. 4,407,957 and 4,409,331 also both to Lim, or U.S. Pat. No. 4,353,888 to Sefton, the disclosures of which are incorporated herein by reference, and many other.

Basically, the above-mentioned interfacial polymerization techniques can be characterized as forming an aqueous dispersion or emulsion of fine size droplets—in which droplets the biocatalyst is itself dissolved or suspended—in a continuous phase of a hydrophobic liquid medium, at least one of the aqueous phase and continuous phase including therein permselective membrane material or permselective membrane precursor material whereby the permselective membrane forms at the interface of the dispersed aqueous phase and the continuous phase whereby the biocatalyst is encapsulated within a barrier formed by the permselective membrane.

In applying any of these interfacial polymerization techniques to the microsphere encapsulated biocatalysts of this invention, the "droplets" are formed by the microspheres, per se, or at least the liquid carrier medium present therein. This feature provides another advantage of the present invention, namely, that since all of the microspheres are of uniform size, wall thickness, etc., all of the "droplets" are likewise of uniform size (diameter). An additional advantage is that it is not necessary or essential to form an emulsion in order to carry out the interfacial polymerization.

In the encapsulation process of the above mentioned patents to Lim and Moss a two step interfacial polymerization process is provided. According to this procedure an emulsion is formed wherein the discontinuous phase (droplets) contains the substance (biocatalyst) to be encapsulated and a first polymerizable monomer. A second monomer which is reactive with the first monomer is added to the continuous phase and an imperfect membrane forms about the droplets of the discontinuous phase. The continuous phase is removed to terminate the polymerization and the partially encapsulated droplets are resuspended in a liquid to which an additional amount of the second monomer is added causing further polymerization, strengthening the permselective membrane, and "patching" any microporous defects.

The Lim and Moss encapsulation process is useful where the biocatalyst is, for example, an enzyme, hemoglobin, antibody, or other "non-living" biochemically active substances. For encapsulation of living microorganisms, cells, cell tissues, and the like the process of the Lim patents or Sefton, for example, is preferred.

According to the above-mentioned patents to Lim encapsulation of the core material (e.g. living tissue, individual cells, etc.) is carried out by suspending the core material in an aqueous medium which contains a water soluble gum that can be reversibly gelled to form a coherent shape-retaining mass, forming the suspension into droplets, changing the conditions of temperature, pH or ionic conditions to cause gellation of the gum to form a temporary protective barrier, and thereafter forming a permanent semipermeable membrane by any suitable technique about the temporary capsules.

Sefton encapsulates live animal cells in a polymeric permselective membrane by first preparing an aqueous suspension of viable cells and bringing the aqueous suspension into contact with a solution of a bio-compatible, water-insoluble polymer in a polar, non-toxic liquid, optionally also in the presence of a water immiscible suspending medium, and forming a suspension of aqueous droplets containing the viable cells in a hydrophobic liquid medium continuous phase. The polymer is caused to precipitate either by addition to the mixture of an additional non-solvent for the polymer or substantially spontaneously due to the non-solvent character of the suspending medium. The precipitated polymer forms the semipermeable membrane encapsulating the cells in the droplets.

Any of the above or any other known encapsulating technique can be used in the present invention. For example, to apply the technique of Lim and Moss to the present invention it is merely necessary to incorporate the first monomer in the liquid carrier medium with the biocatalyst. After the microspheres are filled with the liquid medium—biocatalyst—monomer system the filled microspheres are separated from the remaining (external) liquid medium—biocatalyst—monomer system and are resuspended in the same or different liquid medium to which the second monomer is added. As soon as the second monomer diffuses into the intracapsular space via the entrance means and pores of the microspheres, the first and second monomers will react to form a permselective membrane sealing the pores and openings and thereby providing a protective barrier for the biocatalyst contained within the microsphere.

The technique of Lim can be applied to the filled microspheres by incorporating in the liquid medium—biocatalyst system the water soluble reversible gel forming substance. Then, after transferring the filled microspheres to a liquid medium not containing any of the gel forming substance (or biocatalyst), the conditions in the media are modified to cause gellation of the gel forming substance, at least in the pores and openings in the walls of the microspheres. This can conveniently be accomplished by, for example, using a water-soluble gum having acid groups as the reversible gel forming substance and adding a solution of multivalent cations to the liquid medium. As the multivalent cations diffuse through the entrance means and pores in the walls of the microspheres and contact the gum the gum is rendered water-insoluble, i.e. is gelled, to effectively plug the pores and entrance means and provide a temporary protective barrier for the biocatalyst. Thereafter, a permanent selective membrane is deposited, by any convenient technique which is not detrimental to the biocatalyst, on the gel plugs. As disclosed, for example, in the Lim U.S. Pat. No. 4,352,883, the permselective membrane may be formed by interfacial polymerization using a pair of at least difunctional mutually reactive monomers (as in the Lim and Moss U.S. Pat. No. 4,324,683), or one monomer and a relatively low molecular weight polymer; or by interfacial polymerization using polyaddition reactions; or by permanently cross-linking surface layers of the gel by subjecting them to an aqueous solution of a polymer containing groups reactive with functionalities in the gel molecules.

The encapsulation technique disclosed by Sefton can be adapted to the filled microspheres according to the present invention by suspending the filled microspheres in a polymer solution and adding to the suspension an additional non-solvent for the polymer causing the polymer to precipitate on the microspheres and form a permselective membrane. Preferably, however, the permselective membrane formation is limited to within the entrance means and pores in the walls of the microspheres by including in the liquid medium—biocatalyst system an additional suspending medium which is a non-solvent for the polymer. Then when the microspheres filled with the liquid medium-biocatalyst-non-solvent suspending medium is contacted with the polymer solution the polymer can diffuse into the entrance means and pores of the wall and will precipitate as a thin film as soon as it contacts the non-solvent suspending medium.

According to one preferred technique, a permanent semi-permeable membrane material is formed across the entrance means and pores by washing the gel protected microspheres in an isotonic salt solution or in deionized water and, thereafter, contacting the washed microspheres with a semi-permeable film-forming material or a precursor thereof, e.g. a prepolymer, oligomer, or monomer system with polymerization catalyst and, optionally a cross-linking agent. The gel may function merely as a support for the polymer film in the pores and macropores or the gel material at the gel surface and the film-forming material may react with each other, such as by cross-linking, to form the semi-permeable film.

Any suitable method can be used for depositing the semipermeable film. For instance, the microspheres can be immersed in a dilute solution of a film-forming polymer or a polymer forming system, preferably while applying mild agitation to the mixture to ensure homogeneity and uniform formation of the film on all of the microspheres. It is also preferred to carry out the contact with a small overpressure on the system to force the polymer film into the pores and macropores, as well as between and among the individual sintered particles of the microsphere walls and defining the pores and macropores, this serving to strengthen the bond between the formed membrane and the microsphere. It should be noted that the application of pressure to the film forming solution in which the microspheres are immersed can be analogized to the application of a vacuum to the bore of hollow porous filaments to which a permselective polymer coating is applied from the exterior, such as taught in U.S. Pat. Nos. 4,230,463, and 4,214,020. The coating process is generally suitable for applying a depositable film forming material to form a deposit of a semi-permeable membrane in the pores and macropores of individual microspheres over essentially the entire surface areas of the hollow microspheres. Any potential for formation of air pockets is reduced or any air pockets which do form can be dissipated by the pressure exerted on the deposited material, as well as by diffusion or permeation of the air pocket into the gel, the surrounding interconnecting voids between the wall forming particles, or through the deposited material itself. The deposited films are sufficiently thin to provide high flux rates of gases, liquids and solutes, having molecular weights below the "cut-off" weight of the deposited semi-permeable film. The "cut-off" weight refers to the maximum molecular weight of dissolved solutes which can diffuse through the semi-permeable membrane.

In further detail, the depositable material, i.e., a material suitable for forming the coating, desirably has a sufficiently large molecular size (if dissolved in the solvent) or a sufficiently large particle size (if suspended in the solvent, say, as a colloidal suspension) that the depositable material does not readily pass through the gel-filled pores in the walls of the hollow microspheres when subjected to pressure. Thus, with microspheres having pores of generally larger diameters, depositable materials which have larger sizes when in the coating liquid are frequently desired. In some instance, it is desirable to employ depositable materials which, when in the liquid substance, have sufficiently small sizes that they can enter, instead of bridge, pores in the microspheres. The depositable material may directly form the coating when deposited, or the deposit of the depositable material may be further treated, e.g. by cross-linking, to form the desired coating.

The coating liquid generally comprises a solvent (or vehicle) for the depositable material. The solvent should be capable of dissolving the depositable material or be capable of enabling a finely-divided suspension of the depositable material, say, having particle diameters less than about 1 micron, e.g. about 5000 angstroms (i.e., colloidal size) to be provided. Desirably, the coating liquid contains substantial amounts of solvent, e.g. a major amount of solvent, such that during deposition of the depositable material on the hollow microsphere, depositable material, which is not forcibly retained in the pores and macropores due to adhesion to the gel and/or solid wall material and/or due to the presence of the applied pressure, can be redissolved or otherwise removed from the vicinity of the hollow microspheres. Also, the coating liquid contains sufficient amounts of solvent such that the coating liquid exhibits a viscosity at temperatures employed in the coating which viscosity is advantageously low to enable relatively rapid, adequate permeation of the coating liquid through a dense mass of the microspheres. Often, the viscosity of the coating liquid at such temperatures is less than about 25 or 50 centipoise, and in some instances less than about 10 centipoise, say, about 0.1 to 5 centipoise. Often, the depositable material comprises less than about 20, preferably, less than about 15, say about 0.1 to 15, weight percent of the coating liquid. Most frequently, the depositable material comprises 0.5 to 10, weight percent of the coating liquid.

The contact of the coating liquid containing the depositable material with the mass of microspheres in order to effect the desired deposition is advantageously provided by immersion of the mass in the coating liquid. The immersion of the hollow microspheres in the coating liquid may be effected in any suitable manner. For instance, the mass of microspheres may be poured into the coating liquid. However, it is generally preferred that the coating liquid be added to a retaining vessel containing the mass of microspheres.

The coating liquid may be unagitated or may preferably be agitated, e.g. by circulating the coating liquid through the retaining vessel to assist in maintaining the suspension of the depositable material (if the depositable material is in particulate form in the coating liquid) and in providing desirable distribution of the coating liquid through the microsphere mass.

The coating liquid may be at any suitable temperature immediately before and during the immersion which is not deleterious to the coating liquid, the gel, biocatalyst or the hollow microspheres. The temperature should be sufficiently high to provide the coating liquid with a desirable viscosity for conducting coating but not unduly elevated such that either the coating liquid, particularly the depositable material, or the biocatalyst, etc., are adversely affected. The temperatures of the coating liquid immediately before and during the immersion are below the boiling point of the coating liquid under the conditions of coating operation, and preferably are within the range of about $-10°$ to $70°$ C., say about $0°$ to $50°$, and most conveniently, about ambient temperature, e.g. about $5°$ to $40°$ C.

The hollow microspheres are subjected to the applied pressure from the exterior to the interior at least while immersed in the coating liquid. The pressure drop is desirably maintained for a time (either intermittent or preferably continuous) sufficient to provide the desired deposit. The pressure drop from the exterior to the interior during the immersion is sufficient to provide the desired deposit of depositable material. Generally, the pressure is at least about 5 pounds per square inch gauge, say, about 5 to 100 or more, pounds per square inch gauge. Although higher pressure drops can be employed, such high pressure drops are not necessary, since often, little, if any, benefit is obtained by increasing the pressure to greater than about 50 pounds per square inch. Preferably, the pressure is about 10 to 50 pounds per square inch. The pressure drop is often maintained for a duration of at least about 0.01 hour, e.g., about 0.05 to 10 or 50 hours, say about 0.05 to 5 hours.

The microspheres are immersed in the coating liquid for a sufficient duration to provide the desired deposition of the depositable material. Generally, the duration of immersion depends on the mass of the microspheres, the packing density of the hollow microspheres, the viscosity of the coating liquid, and the applied pressure. In many instances, the duration of the immersion will be at least about 0.01 hour and may be up to about 50 or more hours, e.g. about 0.05 to 10 hours, say about 0.05 to 5 hours.

Since the gel may often extend to the outer surface of the microsphere wall, that is, completely fill the interstitial spaces between the sintered together particles forming the wall, as well as the macropore volume extending through the wall, it is often preferred in order to increase the bonding or anchoring of the depositable material forming the permselective membrane to the sintered together particles, to displace a portion of the gel at and below the outer wall surface to expose the sintered together particles. This may be accomplished, for example, by reliquefying the outer portion only of the gel, for example, by the technique described below, or by slightly raising the temperature of the system, and thereafter washing out the reliquefied gel before depositing the membrane material. Another method involves adding minute gas bubbles to the system, for example, by application of high frequency agitation to cause cavitation at the surface of the microspheres and displacement of the gel by the bubbles. The agitation may be sonic or acoustic. The amplitude of the vibration will be selected depending on the desired depth of displacement but generally can be about one-eight to one-fourth or more of the thickness of the microsphere wall. Furthermore, if the intracapsular space is not completely filled with the gel material a portion of the gel present in the microsphere wall may be displaceable into the intracapsular space by application of fluid pressure to push the gel out of the interstitial spaces (interconnecting voids) into the intracapsular space.

The emersion of the coated microspheres may be by removing the microspheres from the coating liquid or by preferably draining the coating liquid from the retaining vessel.

After the emersion of the coated microspheres from the coating liquid, the microspheres may be immersed in at least one additional coating liquid, which additional coating liquid may or may not be essentially the same as that of the first coating liquid, in order to provide two or more coatings on the hollow microspheres or to chemically affect at least one preceding deposit, e.g., by cross-linking or the like. Cross-linking or other procedures which chemically affect the deposit may be provided by contact with a suitable liquid or gaseous agent. The deposits on the hollow microspheres may or may not be dried (i.e. the remaining solvent removed) or otherwise treated intermediate the immersions.

Frequently, after the emersion from the coating liquid, the deposit is dried, i.e., the remaining solvent is removed. The drying can be conducted in any suitable manner. For instance, the microspheres may be air dried or gases which are unsaturated with the solvent may be passed through the mass of the coated microspheres. Preferably, in instances in which the solvent poses a fire risk, the drying gases are substantially inert such as nitrogen, carbon dioxide, etc. The temperature of the drying gases may vary substantially provided that the desired drying occurs and the material deposited and the encapsulated biocatalyst are not unduly adversely affected. For the sake of convenience, the drying gases may be at slightly elevated temperatures, e.g. about $30°$ to $70°$ C. The drying is generally conducted for a time sufficient to remove substantially all of the solvent from the coating, e.g. often about 1 to 48 hours. After drying, the deposit on the exterior surfaces of the hollow microspheres is sufficiently nontacky that no undue sticking of the hollow microspheres occurs.

The depositable material which is deposited may not directly form the desired coating but rather may be a precursor for the coating. Thus, the depositable material may be capable of reacting with one or more simultaneously or subsequently provided components, or it may be capable of homopolymerizing, to provide the desired coating. Therefore, conditions are provided during the drying and/or subsequent to the drying to chemically convert the depositable material to the desired material of the coating. Hence, coatings can be provided that are comprised of materials which materials would not be desirable as depositable materials.

The resulting coating (or coatings) are relatively uniform throughout all the pores and interconnecting voids and macropores. Generally, the coating has an average thickness of up to about the wall thickness, preferably about ½ to 1/50 of the wall thickness. Frequently, the average thickness of the coating is less than about 5, and may even be about 1 micron or less. Advantageously, the coating is substantially permanent in the pores and interconnecting voids and macropores and thus does not unduly separate from the hollow microsphere during storage or use of the bioreactors in biotech operations.

The hollow microspheres prior to being coated are porous, i.e. have continuous channels for fluid flow extending between the exterior and interior surfaces. Frequently, the pores have an average cross-sectional diameter of from about 5000 to about 40,000 angstroms (0.5 to 4 microns) and in some hollow microspheres, the cross-sectional diameter of the pores or interconnecting voids may be less than about 1000 or more than about 50,000 angstroms.

Passage across the semipermeable membrane may be by chemical or molecular diffusion and/or by solvation and evaporation and is dependent on the molecular spacing of the coating material.

In a preferred embodiment for carrying out the encapsulation of the biocatalyst, especially living cells and microorganisms (hereinafter jointly referred to for convenience as "cells" or "cellular biocatalyst,") in the microsphere container, the following sequence of steps is carried out:

1. A homogeneous suspension of the cellular biocatalyst in a solution of a long-chain polyanion gel former is prepared.
2. The macropore containing microspheres are filled with the cellular biocatalyst suspension using hydrostatic pressure, centrifugal forces, etc.
3. The filled microspheres are contacted with a physically compatible multivalent ion to replace the monovalent ion of the gel former to cross-link the latter and form a temporary discontinuous gel membrane.
4. A permanent membrane is deposited on the gel membrane surface by appropriate reaction and polymerization.
5. The temporary gel membrane is removed by contact with a monovalent ion solution leaving intact the permanent permselective membrane.

These steps will be described in greater detail below.

Step 1. Biocatalyst Suspension

Healthy cells with a viability of greater than 95% are first collected by centrifugation. The cell pellet is then resuspended in the presence of additional components, which are defined as those specific protein or other components which need to remain closely associated with the cells to either promote growth or aid in the production and secretion of the specific macromolecules.

The nutrient medium employed will be dependent upon the cellular biocatalyst involved and the product desired or purpose for the reactor. For example, the nature of the nutrient medium will be adapted to the particular type of cells or microbes. Besides nutrients, other substances may be included to support growth and/or cell differentiation or to provide a particular product.

The cells are incubated in a nutrient cell culture medium under cell growth maintenance conditions of pH and temperature. Suitable nutrient cell culture media are known to the art and such may be used in the method of the present invention. Typically such nutrient culture media contain the known essential amino acids, vitamins, carbohydrates, mineral salts and, preferably, blood serum. Fungicides and bacteriacides may also be included in such media in desired amounts to prevent the growth of undesired microorganisms. As indicated above the pH of the nutrient medium is advantageously controlled within the desired range (typically in the range of 6.8–8.2) by including small amounts of carbon dioxide in the oxygen carrier. However, if desired the pH can be controlled by including a suitable buffer such as HEPES buffer (a mixture of N-2-hydroxyethyl piperazine and N'-2-ethane sulfonic acid) in the nutrient cell culture medium itself. Other suitable methods for controlling pH such as passing the medium over ionic exchange resins may also be employed. The resulting cell slurry is then combined with 1.2–1.4% (v/v) solution of alginic acid or other gel-former in isotonic saline.

Step 2. Filling microspheres (Droplet Formation)

The macropore containing hollow rigid microspheres (preferably formed from inorganic solid particles) prepared in accordance with the techniques disclosed in the aforementioned application Ser. No. 639,126, now U.S. Pat No. 4,671,909 are loaded into one or more centrifuge tubes and the cell slurry prepared in step 1 is added to the tube or tubes. The diameter of the macropores will be selected to be at least 2 times, preferably from about 2 to 5 or more times the major dimension of the cellular biocatalyst.

The centrifuge tube is rotated at a rate sufficient to provide dynamic pressures within the ranges described above, until the microspheres are filled with a liquid "microdroplet" containing the viable cellular biocatalyst distributed homogeneously throughout the microdroplet at a density determined by the initial ratio of cells to sodium alginate.

Step 3. Gel Formation

The rigid microsphere housed liquid microdroplets are recovered from the centrifuge tubes and are added to a solution of divalent or multivalent cations. Calcium ions are the preferred divalent cations for gelling sodium alginate. A calcium alginate gel which is shape-retaining is formed in at least the pores and macropores and generally, also in its interior, the liquid microdroplet is converted to a shape-retaining fluid permeable gel which is harmless to the entrapped cellular biocatalyst.

Step 4. Semipermeable Membrane Formation

The gel entrapped cellular biocatalyst protected by the rigid microsphere containers are next contacted with a saline solution containing a long-chain polycation. Some of the long-chain polycations used in this membrane formation step include polymers of the L-amino acids, lysine, argine, ornithine, polymers of the D-amino acid lysine, and synthetic organic polymers such as polyethyleneimine and polyvinylamine. Interaction of the polycation with the surface of the calcium alginate gel results in the formation of a tight mixed-gel membrane which has defined permeability characteristics.

Immediately following formation of the semipermeable membrane, the resulting microsphere bioreactors are washed with a saline solution containing a dilute concentration of a long-chain polyanion. This reaction neutralizes the high positive charge density imparted to the surface of the membrane due to the presence of the coating polycation. Following this step, the membranes display a net neutral surface charge behavior.

Step 5. Liquefication of the Microdroplet Interior

Following the deposition of the membrane at the surface of the calcium alginate gel, the resulting bioreactor is treated with a chelating agent capable of sequestering the gel-catalyzing cation, but not capable of disrupting the interaction between the long-chain polycation and the surface alginic acid. The resulting chelation, in the presence of excess sodium ions, results in conversion of the calcium alginate gel to sodium alginate. Depending on the molecular weight of the sodium alginate used in the initial cell suspension, a predetermined percentage of the sodium alginate diffuses from the intracapsular space to the extracapsular space, thereby decreasing the absolute intracapsular concentration of alginic acid, and leaving behind the "permanent" semipermeable membrane.

The parameters which affect the permeability of the semipermeable membrane include the following:
1. The concentration of the coating polycation.
2. The molecular weight of the coating polycation.
3. The secondary structure of the coating polycation.
4. The duration of the reaction.
5. The temperature under which the reaction takes place.

The permeability of the microcapsule membrane is generally expressed in terms of the molecular weight of globular polypeptides. Using this system of measurement, membrane permeabilities can be obtained in the range of <50,000 daltons to >900,000 daltons. A preferred molecular weight cut-off limit is about 300,000 daltons, especially about 200,000 daltons.

Following liquefaction, the bioreactors will be washed several times with a clear saline solution. The bioreactors are then ready for use in a biotech process.

Naturally, other techniques for forming the permselective membrane at least in and across the entrance means and pores/channels in the walls of the microspheres can be used, so long as the permselective membrane can be formed and/or deposited under conditions which are nondetrimental to the continuing viability or activity of the biocatalyst.

Advantages

The permselective membrane coated microspheres provide a sterile nutrient environment for the biocatalyst contained therein. In comparison to the bioreactors formed by encapsulating biocatalysts in polymeric microspheres, such as described in the above-mentioned patents to Lim, Lim and Moss or the patent to Sefton, wherein the polymer walls provide the joint function of permselective membrane and support structure, the bioreactors of the present invention have the important advantage of uncoupling the structural support function from the selective separation function. Accordingly, the permselective membranes can be much thinner than the wall thickness of the prior art microcapsules with correspondingly higher flux rates, while still providing much greater overall strength. For example, the permselective membrane coated microspheres of this invention can withstand hydrostatic pressure up to at least about 1500 psi, and two point pressures up to at least about 200 psi. In view of this high wall strength, the bioreactors are much more easily handleable and transferable and can be used in fixed bed processes at high packing densities, for example, bed heights of up to 30 feet or more, and in fluidized bed processes wherein bioreactor-to-bioreactor contact or bioreactor-to-tower wall impacts even at high speeds do not cause any structural damage to the microsphere walls or stress to the permselective membranes. Furthermore, the generally low density and mass of the microsphere containers contributes to this advantage and also reduces the shear and impact forces which could be harmful to certain biocatalysts.

Because of their exceedingly low cost, the permselective membrane coated microspheres can be discarded periodically for short lifetime membrane materials or they can be recycled for regeneration of the permselective membrane and/or for renewal and/or collection of the biocatalyst and/or collection of product.

In addition, the bioreactors of this invention are much more uniform in size than the prior art microcapsule bioreactors. Furthermore, a much wider range of diameters and wall thicknesses are available for the hollow porous rigid microsphere containers than for the liquid microdroplets used in the conventional encapsulating techniques. Therefore, control of process parameters, e.g. mass flow rates, fluid dynamics, heat transfer, etc., is greatly simplified.

Because the microspheres are hollow and have porous walls, they will generally have bulk densities which are significantly lower than the density of the solid particles forming the microsphere walls, e.g. in the range of from about 0.02 g/cm$^3$ to about 2.4 g/cm$^3$, preferably from about 0.03 g/cm$^3$ to about 1 g/cm$^3$, and, therefore, when filled will approximate the density of the aqueous systems used in most biotech processes, and therefore, the bioreactors, i.e. microsphere encapsulated biocatalysts, will be buoyant or at least easily suspended in the aqueous culture broth or other liquid medium, e.g. aqueous waste stream, etc., used in the biotech process. The bulk density of the bioreactors will not be significantly increased by the permselective membrane since the material of the permselective membrane will generally have a lower density than that of the solid particles, and/or because the permselective membranes are generally substantially thinner than the microsphere wall thickness.

Still, another advantage of the bioreactors of this invention is that the microsphere containers, while nondeformable under conditions of use in the biotech processes, can be broken where necessary or desired for removal and/or recovery of the biocatalyst and/or products, etc. The microsphere wall will absorb substantially the entire amount of pressure exerted to effect the rupture of the wall without adversely effecting the biocatalyst and/or product. In contrast, prior art microcapsules which have relatively soft and deformable walls will require very high pressures to cause rupture and will also transmit these high pressures to their contents.

Furthermore, the preceding advantages apply equally to the gel-immobilized biocatalyst encapsulated within the rigid microsphere wall structure.

Biotech Processes

As used herein the term "biotech" process is given as broad a meaning as possible consistent with the requirement that it involves the use of at least one reactant or substrate which is modified, converted, altered, concentrated, adsorbed, desorbed, or otherwise reacted, more or less specifically, through the assistance of a biocatalyst in order to manufacture, purify, separate, identify or quantify particular chemical and biological substances.

Thus, biotech processes encompass such diverse technologies as fermentation processes, biological waste water treatment, cell culture techniques, enzyme and bacterial catalyzed biochemical reactions, protein binding assays, drug delivery systems, affinity chromatography, and the like. Cell culture techniques include both growth of cells into cell tissues or cell masses for use as such, as well as growth and/or maintenance of cells for production of cell products such as hormones, enzymes, amino acids, nucleic acids, nucleotides, nucleosides, phosphatides, glucosides, purines, interferons, lymphokines, growth factors, and other biological substances.

Virtually any of the existing biotech processes can be adapted to advantageously employ the bioreactors of the present invention, regardless of the nature of the biocatalyst.

EXAMPLE 1

This is an example of a fermentation process utilizing the novel bioreactors of this invention for the production of ethanol from fermentative sugar, e.g. glucose, such as by the process described in U.S. Pat. No. 4,350,765 to Chibata, et al using immobilized ethanol-producing microorganisms of the genera Saccharomyces and Zymomonas. The hollow porous alumina microspheres of Example 4 of the aforementioned application Ser. No. 639,126 having an outer diameter of about 2500 microns (2.5 mm) and a wall thickness of about 20 microns, with entrance means (macropores) of about 25 microns in diameter extending through the wall thickness, and an average pore diameter of from about 0.1 to 3 microns are used as the bioreactor container. To fill the hollow microspheres with the microbes, a suspension of the microbes, for example, Sacch. sake ATCC 26422 (Japan strain Kyokai 7), in a gel forming carrier, such as a sterilized 4.5w/v % aqueous solution of carragenan (manufactured by the Copenhagen Pectin Factory, Ltd. under the tradename "GENUGEL Type WG") at a concentration of about one loopful per 20 ml is placed in a centrifuge tube maintained at about 37° C. The hollow microspheres, after sterilization if necessary, in an amount of about 50% to about 65% by bulk volume based on the volume of the gel forming carrier, are added to the centrifuge tube and the mixture is centrifuged at about 5 psig for about 200 minutes. The excess gel forming carrier is decanted off from the filled microspheres and the filled microspheres are then added to an about 2 w/v % aqueous solution of potassium chloride whereby a gel forms in at least the entrance means and pores to seal in the microbes.

After washing the microspheres with the gel entrapped yeast contained therein with a sterile aqueous saline solution, the bioreactors are ready for use.

A nutrient broth is prepared by admixing a yeast extract (0.15 w/v %), ammonium chloride (0.25 w/v %), dipotassium hydrogenphosphate (0.55w/v %), magnesium sulfate heptahydrate (0.025 w/v %), calcium chloride (0.001 w/v %) citric acid (0.1 w/v %) and sodium chloride (0.25 w/v %) in water and adjusting the pH thereof to 5.0.

The bioreactor containing the gel-immobilized yeast (20 ml) is contacted with the nutrient broth containing 10 w/v % of glucose (20 ml) at 30° C. for 1 hour. When the concentration of the remaining glucose in the broth is lowered to 2 mg/ml, the additional fresh nutrient broth containing 40 w/v % of glucose (5 ml) is added and the conversion reaction of glucose into ethanol is continued for another 1 hour under the same condition. Thereafter, the addition of the nutrient broth containing 40 w/v % of glucose (5 ml) is repeated 3 times at an hour-intervals. As a result, the immobilized yeast keeps its ethanol-producing activity at the level of 50 mg/ml of the gels/hr during the reaction period and the broth containing ethanol in a concentration of 125 mg/ml (40 ml) is obtained after the conversion reaction for 5 hours.

EXAMPLE 2

Using the same microsphere bioreactors as produced in Example 1, ethanol production is carried out using a cylindrical columnar reactor. A column having a circulating tube which is able to circulate a portion of a broth flowed through column 1 to the bottom of the column is prepared by packing the bioreactors (2.5 liters) into the column, feeding 20 w/v % of an aqueous molasses solution (100 mg/ml as glucose) to the bottom of the column through a broth feeding pipe at the rate of 2.5 liter/hr at 30° C. to float the bioreactors in the column and flowing out the broth from the top of the column through an outlet pipe at the same rate. After incubation at 30° C. for 40 hours while feeding the broth at the above feed rate, 50 w/v % of the aqueous molasses solution (250 mg/ml as glucose) is fed to the column at a rate of 1 liter/hr while a portion of the broth flowed through the column is circulated to the bottom of the column through the tube circulating at a rate of 10 liter/hr. The concentration of the aqueous molasses circulating through the tube is lowered to not more than 10 mg/ml as glucose. Under this condition, ethanol producing activity of the immobilized yeast is not lowered and an effluent containing ethanol in the concentration of 125 mg/ml is continuously flowed out from the outlet pipe at the top of the column since the concentration of the aqueous molasses in the broth to be fed to the column is diluted with the circulated broth through the tube.

EXAMPLE 3

Islets of Langerhans obtained from rat pancrease are added to a complete tissue culture (CMRL - 1969 Connaught Laboratories, Toronto, Canada) at a concentration of approximately $10^3$ islets per milliliter. The tissue culture contains all nutrients needed for continued viability of the islets as well as the amino acids employed by the Beta cells for making insulin. Four milliliters of the islet suspension are then added to five milliliters volume of 1.2 percent sodium alginate (Sigma Chemical Company) in physiological saline.

Following the teachings of the hollow porous microsphere manufacturing process of application Ser. No. 639,126, microspheres having a diameter of about 5000 microns and a wall thickness of about 100 microns and containing in their walls a plurality of macropores of about 200 microns, are prepared.

Two 20 ml centrifuge tubes are each filled with 4 ml of the hollow microsphere containers and the culture-medium tissue suspension in two equal portions of 4.5 ml each are added to the centrifuge tubes. The tubes are rotated at 600 rpm for 45 seconds and the excess culture-medium tissue suspension is decanted off and the culture-medium tissue suspension filled microsphere are recovered.

Next 800 milliliters of a 1.5% $CaCl_2$ solution are placed in a 1.5 liter beaker equipt with a stirrer and the hollow porous rigid microspheres filled with the culture-medium tissue suspension are slowly introduced into the $CaCl_2$ solution whereupon the sodium alginate in the macropores and smaller pores immediately begins to gel.

After 10 minutes, the stirrer is turned off and the supernatant solution is removed by aspiration. The microspheres are then transferred to a beaker containing 150 ml of solution comprising one part of a 2% 2(cyclohexylamino) ethane sulfonic acid solution in 0.6% NaCl (isotonic, pH=8.2) diluted with 20 parts 1% $CaCl_2$. After a 3 minute immersion, the microspheres are washed twice in 1% $CaCl_2$.

The microspheres are then transferred to a solution comprising 1/80 of one percent polylysine (average MW 35,000 AMU) in physiological saline. After 3 minutes, the polyslysine solution is decanted. The microspheres are then washed with 1% $CaCl_2$, and then suspended for 3 minutes in a solution of polyethyleneimine (MW 40,00060,000) produced by diluting a stock 3.0% polyethyleneimine solution in morpholino propane sulfonic acid buffer (0.2 M, pH=6) with sufficient 1% $CaCl_2$ to result in a final polymer concentration of 0.10%. The resulting microspheres have permanent semipermeable membranes extending across the macropores and pores at the exterior wall surface. The resulting bioreactors are then washed twice with 1% $CaCl_2$, twice with physiological saline, and mixed with 100 ml of a 0.12 percent alginic acid solution.

The microspheres resist clumping and contain islets of Langerhans. Gel on the interior of the capsules is reliquified by immersing the microspheres in a mixture of saline and critrate buffer (pH=7.4) for 5 minutes. Lastly, the capsules are suspended in CMLR - 69 medium.

Under the microscope, the microcapsules have an appearance illustrated in the FIG. 4. They comprise an ultrathin membrane 44 extending within the macropores and pores near the outer periphery of the microsphere wall. One or more islets 54 each consisting of many individual cells are suspended in the liquid culture medium 55 in the intracapsular space 50 and are protected against attack by bacteria, viruses and other microbes. However, molecules having a molecular weight up to about 100 thousand can traverse membrane 44. This allows oxygen, amino acids, nutrients, and plasma components used in culture media (e.g. fetal calf plasma components) to reach the islet and allows insulin to be excreted.

Similar results to the above are achieved with other cellular biocatalysts, for example, red blood cells using serum as a medium, sperm cells, using semen as the medium, and baker's yeast.

Cell cultures encapsulated as described above may be suspended in culture media designed specifically to satisfy all of the requirements of the particular cell type involved and will continue to undergo normal in vitro metabolism. If the culture requires an environment of high molecular weight components such as serum components, these may be omitted from the extracapsular medium. Typically, the components normally ingested by cells are of relatively low molecular weight and readily diffuse across the capsule membranes into the microenvironment of the cells where they permeate the cell membrane. Products of metabolism of the cells which are secreted into the intracapsular medium, if they have a molecular weight below the upper limit of permeability of the capsule membrane, likewise diffuse thereacross and collect in the extracapsular medium.

The encapsulated cells may be cultured under conditions of, e.g. temperature, pH and ionic environment, identical to conventional cultures. Also, cell-produced products may be harvested from the extracapsular medium or from capsules by conventional techniques. However, the culturing technique disclosed herein has the following advantages:

1. The cells of the culture are protected from contamination by factors having dimensions in excess of the upper permeability limit of the membranes. This means that handling and sterility requirements normally incident to culturing procedures can be somewhat relaxed, since microorganisms cannot reach the encapsulated cells, and virus infected cells need not contaminate other cells.
2. The microcapsules in effect immobilize the cells within an environment in which enclosed high molecular weight materials are confined, yet lower molecular weight cell nutrients and products are readily removed and introduced. This allows the nutrient broth to be intermittently or continuously collected and supplemented as desired, without disturbing the cells.
3. Substances of interest produced by the cells are more easily recovered. Secreted cell products of molecular dimensions small enough to permeate semipermeable membranes collect in the extracapsular medium in admixture with nutrients. However, high molecular weight serum components and the like are not released into the extracapsular medium, thus simplifying recovery of a cell product of interest. Secreted cell products of molecular dimensions in exces of the upper permeability limit of the membranes collect within the capsules. Of course, cell products not secreted through the cell membrane may also be of interest. These may be recovered in relatively concentrated form by isolating the microspheres and subsequently selectively disrupting the membranes using, for example, the technique disclosed hereinafter, and if necessary by disrupting the cell membranes.
4. The intracapsular volume provides an environment well suited for cell division. Suspension cultures undergo mitosis within the microspheres. Anchorage dependent cells which in normal cultures grow in a two-dimensional monolayer multiply to form an array within the microsphere. Such cells use the interior surfaces of the membrane as a substrate and/or anchor to the solid particulate wall forming materials set forth above. This leads to significant increases in cell density as compared with conventional cultures. The ongoing viability of such cell clusters is aided by the fact that the surface area to volume ratios of the capsules can be quite large, and thus, all cells have access to required nutrients, oxygen, etc.
5. The solid rigid walls provide all the required structural support for and protect the semipermeable membrane from shearing forces and mechanical damage. Therefore, the semipermeable membranes can be substantially thinner than in conventional semipermeable membrane microcapsules wherein the membranes also provide the structural support. This allows the bioreactors of this invention to be used at much larger packing densities, in long columns, in high rate continuous flow and fluidized bed processes and the like.

In certain situations, it would be advantageous to selectively disrupt the membranes to release the cells without damage. One notable example is in the production of interferon (INF). Cells capable of producing INF must be subjected to certain viruses or nucleic acids in preparation for the INF production stage. Also, in several INF induction procedures, reagents are added to the culture to inhibit protein synthesis. Accordingly, the growth stage of the culturing process must be conducted under conditions quite different from the INF induction stage. If the substances used for INF induction are of a molecular weight in excess of the upper permeability limit of the capsule membranes (as will be the case in virus inductions), the induction process cannot be accomplished in the encapsulated cell culture. Accordingly, IFN producing cells, if grown within the microcapsules, would have to be releasedby disruption of the membrane in order to be subjected to the induction process.

Cells confined in microspheres sealed with semipermeable membranes of the type set forth above may be released by a process involving commercially available reagents having properties which do not significantly adversely affect the encapsulated cells. First, the microspheres are separated from their suspending medium, washed thoroughly to remove any contaminants present on the exterior of the microspheres, and then dispersed with agitation, in a mixed solution of monatomic, multivalent cations, such as calcium ions and a stripping polymer having plural anionic moieties, such as a salt of a polysulfonic or polyphosphoric acid. Heparin, a natural sulfonated polysaccharide, is preferred for this step. The anionic charge density of the stripping polymer used should be equal to or preferably greater than the charge density of the polyanionic material originally employed to form the membranes. The molecular weight of the polymer should be at least comparable to and preferably greater than the molecular weight of the polymer having plural cationic groups used in forming the membrane. Within the suspension of microspheres in the mixed solution, the calcium ions compete with the polycationic polymer chains used to form the membrane for anionic sites on the water-soluble gum. Simultaneously, the heparin or other polymer having plural anionic moieties dissolved in the solution competes with the gum in the membrane for cationic sites of the polymer chains. This results in a water-dispersable or preferably water-soluble complex of e.g. polylysine and heparin, and an association of the monatomic cations with molecules of the gel.

This step renders the membrane susceptible to dissolution upon subsequent exposure to a sequestering agent which completes the disruption process by taking up monatomic ions from the gel. Capsule membrane debris which remains in the medium, if any, can be easily separated from the cells which are allowed to diffuse or flow with the medium through the now unblocked macropores to the extracapsular space.

The currently preferred solution for the first stage of the selective disruption process comprises 1.1% calcium chloride (w/v) and between 500 to 1,500 units of heparin per milliliter of solution. A volume of microspheres is added to this solution sufficient to constitute between about 20% and 30% of the total volume of suspension. Calcium chloride and heparin are preferred for disrupting membranes of cell-containing microspheres since both reagents are physiologically compatible with most cells and, therefore, minimize the possibility of cell damage. Mixtures of aluminum salts or other multivalent cations (but not Mg++ ions) may also be used together with the polysulfonic or polyphosphoric acid salts of the type set forth above.

In general, the concentration of monatomic ions and anionic polymer used in this step may vary widely. Optimum concentrations may be readily determined empirically, and depend on exposure time as well as the particular polymer used to form the membranes.

The currently preferred sequestering agent for performing the selective disruption is sodium citrate, although other alkali metal citrate salts and alkali metal EDTA salts may also be used. When sodium citrate is employed, the optimum concentration is on the order of 55 mM. It is preferred to dissolve the citrate or other sequestering agent in isotonic saline so as to minimize cell damage.

EXAMPLE 4

One and one-half ml of an aqueous carrier solution comprising polyvinylpyrrolidone, albumin, and 250 μl of antisera to thyroxine are mixed with 50 μl of 0.5 M tetraethylene pentamine carbonate (pH=8.2-8.6). The aqueous system is mixed by means of a magnetic stirring bar, and as stirring continues, the mixture is added to a pressure vessel containing 15 ml of the hollow porous rigid microspheres used in Example 1 and the pressure is increased to about 150 psi over a period of 60 minutes and is held at 150 psi for an additional 30 minutes. The pressure is then gradually released over a ninety minute period to atmospheric pressure whereupon the excess emulsion is decanted and the filled microsphere are washed 3 times with distilled water. One 20 ml portion of a 4:1 (v/v) cyclohexanechloroform solution containing 0.1 mg/ml teraphthaloyl chloride is added to the filled microspheres to initiate polymerization between the tetraethylene pentamine carbonate and terephthaloyl chloride. Sixty seconds later, another 8 ml of the terephthaloyl chloride solution is added. After a total reaction time of four minutes, the suspension is gently centrifuged and the supernatant liquid discarded. The microspheres are washed with pure cyclohexane and a 50% aqueous TWEEN-20 solution (sorbitan monolaurate) buffered to neutral pH with 0.3 M $NaHCO_3$.

The foregoing procedure results in bioreactors with encapsulated thyroxine antisera having a pore size large enough to allow free passage of thyroxin, which has a molecular weight of about 777 daltons, yet too small to allow leakage of antibody from the interior of the bioreactors.

What is claimed is:

1. A bioreactor comprising rigid hollow porous microspheres of substantially uniform diameter of 200 to 10,000 microns and of substantialy uniform wall thickness of 1 to 1000 microns, the walls of said microspheres comprise sintered together particles which define interconnecting voids within the walls, said microspheres having a single hollow central void forming intracapsular space in the interior of the microspheres and inner and outer microsphere wall surfaces, said interconnecting voids are continuous and extend from the outer wall surface to the inner wall surface, said walls have substantially uniform void content and said interconnecting voids are substantially uniformly distributed in the walls of the hollow microspheres, said walls including entrance means through which biocatalyst can be introduced into the intracapsular space, biocatalyst within the intracapsular space and fluid permeable means extending across said entrance means for immobilizing the biocatalyst within the intracapsular space, said entrance means being larger than the maximum dimension of said biocatalyst.

2. The bioreactor of claim 1 wherein the ratio of wall thickness to outer diameter is in the range of from about 1:4 to 1:500.

3. The bioreactor of claim 1 wherein the microsphere diameter is 1200 to 6000 microns and the wall thickness is 10 to 200 microns.

4. The bioreactor of claim 3 wherein the ratio of wall thickness to outer diameter is in the range of from about 1:10 to 1:300.

5. The bioreactor of claim 1 wherein the microsphere wall is comprised of sintered together inorganic particles.

6. The bioreactor of claim 6 wherein the inorganic particles have a particle size in the range of from about 0.5 to 10 microns.

7. The bioreactor of claim 6 wherein the inorganic particles comprise metal particles.

8. The bioreactor 1 wherein the microsphere container can withstand hydrostatic pressures of about at least 750 psi and two point contact pressures of about at least 100 psi.

9. The bioreactor of claim 1 wherein said biocatalyst is at least one member selected from the group consisting of enzymes, hormones, antibodies, hemoglobin, interferon, and lymphokines, and mixtures thereof.

10. The bioreactor of claim 1 wherein said entrance means comprise pores in the micropheres wall, said pores having an average diameter in the range of from about 0.1 to 3 microns.

11. The bioreactor of claim 1 wherein the entrance means comprises uniform size macropores extending through the thickness of the microsphere wall.

12. The bioreactor of claim 1 wherein said biocatalyst is at least one viable cellular member selected from the group consisting of animal cells, plant cells, yeast, bacteria, viruses, fungi, and algae.

13. The bioreactor of claim 4 wherein said entrance means comprises macropores extending through the thickness of the microspheres wall, and said macropores have a diameter of 5 to 200 microns.

14. The bioreactor of claim 13 wherein said biocatalyst is at least one viable animal cell selected from the group consisting of normal cells, tumor cels, genetically engineered cells, and mixtures thereof.

15. The bioreactor of claim 13 wherein said biocatalyst is at least one viable microbe selected from the group consisting of bacteria and yeast.

16. The bioreactor of claim 1 wherein said fluid permeable immobilizing means includes a gel present at least in the pores and entrance means of the microsphere wall.

17. The bioreactor of claim 1 wherein said fluid permeable immobilizing means comprises a continuous, semicontinuous or discontinuous semipermeable membrane closing-off the entrance means in the wall of the microspheres, the permeability of said membrane being such that the biocatalyst within the intracapsular space of the microspheres is presented from escaping from the microspheres, while liquids, gases and organic molecules of predetermined molecular size which is smaller than the size of the biocatalyst, can enter or leave the intracapsular space via the entrance means by passage across the semipermeable membrane.

18. The bioreactor of claim 17 wherein said semipermeable membrane is formed by interfacial polymerization with the entrance means and pores.

19. The bioreactor of claim 6 wherein the inorganic particles comprise glass particles.

20. The bioreactor of claim 6 wherein the inorganic particles comprise ceramic particles.

21. A bioreactor comprising rigid hollow porous microspheres of substantially uniform diameter of 1200 to 6000 microns and of substantially uniform wall thickness of 10 to 200 microns and a liquid suspension or solution of biocatalyst encapsulated within said microspheres, said microspheres comprising a spherical porous wall comprised of sintered together inorganic particles, said wall having inner and outer wall surfaces and including interconnecting voids which are continuous and extend from the outer surface of the wall to the inner surface of the wall, said wall having substantially uniform void content and said interconnecting voids are substantially uniformly distributed in the walls of the hollow microspheres, said microspheres wall encircling an intracapsular space in the form of a single hollow central void, said intracapsular space being at least 70% fill with the biocatalyst solution or suspension, said microspheres wall further comprising a plurality of macropore openings extending through the thickness of the wall and having a diameter larger than the major dimension of the biocatalyst, and a semipermeable membrane having a thickness less than the thickness of the microspheres wall, said semipermeable membrane extending across the interconnecting voids and the macropores in order to encapsulate the biocatalyst within the intracapsular space, but permitting diffusion of gases, liquids and dissolved or suspended substances having a molecular weight below a predetermined molecular weight cut-off.

22. The bioreactor of claim 21 wherein the microspheres ratio of wall thickness to outer diameter is in the range of from about 1:10 to 1:300, and said microspheres have a porosity of from about 5 to 45%, exclusive of said macropore openings.

23. The bioreactor of claim 21 wherein the macropore openings are substantially uniform in size of 10 to about 200 microns.

24. The bioreactor of claim 21 wherein said sintered particles comprise metal particles.

25. The bioreactor of claim 21 wherein said macropore openings are at least 2 times the major dimension of the biocatalyst.

26. The bioreactor of claim 21 wherein the walls of said microspheres have substantially the same porosity.

27. The bioreactors of claim 21 wherein said biocatalyst is at least one biochemically active material selected from the group consisting of enyzmes, antibodies, hormones, hemoglobin, interferon and lymphokines.

28. The bioreactor of claim 21 wherein said biocatalyst is at least one viable living cellular biocatalyst selected from the group consisting of animal cells, yeast and bacteria.

29. The bioreactor of claim 21 wherein said sintered particles comprise glass particles.

30. The bioreactor of claim 21 wherein said sintered particles comprise ceramic particles.

31. The bioreactor of claim 21 wherein said biocatalyst is a viable living cellular biocatalyst comprising genetically engineered animal cells.

32. A biochemical process for the production, purification, separation, identification or quantification of a substance wherein the substance or a precursor thereof is acted upon by a biolcatalyst to effect said production, purification, separation identification or quantification which comprise contacting a bioreactor
comprising microspheres of substantially uniform diameter of 200 to 10,000 microns and of substantially uniform wall thickness of 1 to 1000 microns, the walls of said microspheres comprising sintered together particles which define interconnecting voids within the walls, said microspheres having a single hollow central void forming intracapsular space, said walls including entrance means through which biocatalyst can be introduced into the intracapsular space in the interior of the microspheres and inner and outer microsphere wall surfaces, said interconnecting voids are continuous and extend from the outer wall surface to the inner wall surface, said walls have substantially uniform void content and said interconnecting voids are substantially uniformly distributed in the walls or the hollow microspheres, biocatalyst within the intracapsular space and fluid permeable means extending across said entrance means for immobilizing the biocatalyst within the intracapsular space, said entrance means being larger than the maximum dimension of said biocatalyst, with a fluid medium containing at least one low molecular weight substance which is reactive with the biocatalyst and which can diffuse through the fluid permeable immobilizing means into the intracapsular space.

33. The biochemical process of claim 32 wherein a biological substance is produced and wherein said hollow porous microspheres comprise semipermeable immobilizing membranes across said entrance means and the hollow porous microspheres are maintained in contact with a nutrient culture medium for the biocatalyst.

34. The biochemical process of claim 33 wherein the semipermeable membrane has a molecular weight cut-off size of about 200,000 daltons and wherein any nutrients required for the maintenance and/or growth of the biocatalyst which have a molecular weight greater than 200,000 daltons are initially present within the intracapsular space.

35. The biochemical process of claim 32 wherein the microspheres entrance means comprises macropores which extend through the microspheres wall, and said macropores have a diameter of 5 to 200 microns.

36. A bioreactor comprising porous microspheres of substantially uniform diameter of 200 to 10,000 microns and of substantially uniform wall thickness of 1.0 to 1000 microns, the walls of said microspheres comprise sintered together particles which define interconnecting voids within the walls and a single hollow central void forming intracapsular space in the interior of the microspheres and inner and outer microsphere wall surfaces, said interconnecting voids are continuous and extent from the outer wall surface to the inner wall surface, said walls have substantially uniform void content and said interconnecting voids are substantially uniformly distributed in the walls of the hollow microspheres, said wals include entrance means through which biocatalyst can be introduced into the intracapsular space, biocatalyst within the intracapsular space and semipermeable membrane means extending across said entrance means for immobilizing the biocatalyst within the intracapsular space, said entrance means being larger than the maximum dimensions of said biocatalyst, and said microsphere walls are free of latent solid or liquid blowing gas materials and are substantially free of relatively thinned wall portions or sections and bubbles.

37. The biocatalyst of claim 36 wherein the microspheres are of substantially uniform diameter of 500 to 600 microns and are of substantially uniform wall thickness of 5 to 400 mocrons.

38. The biocatalyst of claim 37 wherein the microspheres wall comprises macrospores which extend through the microspheres wall and the microspheres are substantially spherical in shape.

39. A bioreactor comprising hollow porous microspheres and a liquid suspension or solution of biocatalyst encapsulated within said microspheres, said microspheres are of substantially uniform diameter of 1200 to 6000 microns and are of substantially uniform wall thickness of 10 to 200 microns, the walls of said microspheres comprise sintered together inorganic particles which define interconnecting voids within the walls and an intracapsular space in the form of a single central void and inner and outer microsphere wall surfaces, said interconnecting voids are continuous and extend from the outer wall surface to the inner wall surface, said walls have substantially uniform void content and said interconnecting voids are substantially uniformly distributed in the walls of the hollow microspheres, said intracapsular space being at least partially filled with the biocatalyst solution or suspension, said microspheres wall further comprising a plurality of substantially uniform size macropore openings which extend through the thickness of the wall and said macropores having a size larger than the major dimension of the biocatalyst, and a semipermeable membrane extending across the interconnecting voids and the macropores in order to encapsulate the biocatalyst within the intracapsular space, but permitting diffusion of gases, liquids and dissolved or suspended substances having a molecular weight below a predetermined molecular weight cutoff, and said microsphere walls are free of latent solid or liquid blowing gas materials and are substantially free of relatively thinned wall portions or sections and bubbles.

40. The bioreactor of claim 39 wherein the macropore openings are 10 to 200 microns.

41. The bioreactor of claim 39 wherein the microspheres are substantially spherical in shape.

42. A biochemical process for the production, purification, separation, identification or quantification of a substance wherein the substance or a precursor thereof is acted upon by a biocatalyst to effect said production, purification, separation or quantification which comprises contacting a bioreactor
comprising hollow porous microspheres of substantially uniform diameter of 1200 to 6000 microns and of substantially uniform wall thickness of 10 to 200 microns, the walls of said microspheres comprise sintered together particles which define interconnecting voids within the walls and a single hollow central void forming intracapsular space in the interior of the microspheres and inner and outer microsphere wall surfaces, said interconnecting voids are continuous and extend from the outer wall surface to the inner wall surface, said walls have substantially uniform void content and said interconnecting voids are substantially uniformly distributed in the walls of the hollow microspheres, said walls include entrance means through which biocatalyst can be introduced into the intracapsular space, biocatalyst within the intracapsular space and semipermeable membrane means extending across said entrance means for immobilizing the biocatalyst within the intracapsular space, said entrance means being larger than the maximum dimensions of said biocatalyst, and said microsphere walls are free of latent solid or liquid blowing gas materials and are substantially free of relatively thinned wall portions or sections and bubbles, with a fluid medium containing at least one low molecular weight substance which is reactive with the biocatalyst and which can diffuse through the semipermeable membrane immobilizing means into the intracapular space 43. The biochemical process of claim 42 wherein said entrance means comprise a plurality of substantially uniform size macropore openings of 10 to 200 microns size which extend through the wall of the microspheres.

44. The biochemical process of claim 42, wherein a biological substance is produced and wherein said hollow porous microspheres are maintained in contact with a nutrient culture medium for the biocatalyst.

* * * * *